(12) United States Patent
Gottesdiener et al.

(10) Patent No.: US 7,893,091 B2
(45) Date of Patent: Feb. 22, 2011

(54) COMBINATION THERAPY FOR THE TREATMENT OF URINARY FREQUENCY, URINARY URGENCY AND URINARY INCONTINENCE

(75) Inventors: Keith M. Gottesdiener, Scarsdale, NY (US); Stuart A. Green, East Brunswick, NJ (US); Euan MacIntyre, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 152 days.

(21) Appl. No.: 12/083,034

(22) PCT Filed: Sep. 29, 2006

(86) PCT No.: PCT/US2006/038419
§ 371 (c)(1), (2), (4) Date: Apr. 3, 2008

(87) PCT Pub. No.: WO2007/044296
PCT Pub. Date: Apr. 19, 2007

(65) Prior Publication Data
US 2009/0270406 A1    Oct. 29, 2009

Related U.S. Application Data

(60) Provisional application No. 60/723,547, filed on Oct. 4, 2005, provisional application No. 60/779,144, filed on Mar. 3, 2006.

(51) Int. Cl.
*A61K 31/4406* (2006.01)
*A61K 31/137* (2006.01)
(52) U.S. Cl. ........................ 514/342; 514/648
(58) Field of Classification Search ........................ None
See application file for complete search history.

(56) References Cited

U.S. PATENT DOCUMENTS

2004/0248979 A1 * 12/2004 Brettman et al. ............ 514/561

FOREIGN PATENT DOCUMENTS

| WO | WO 98/32753 A1 | 7/1998 |
|---|---|---|
| WO | WO 2005/032464 A2 | 4/2005 |
| WO | WO 2005/073191 A1 | 8/2005 |
| WO | WO 2006/002117 A1 | 1/2006 |

* cited by examiner

*Primary Examiner*—Phyllis G. Spivack
(74) *Attorney, Agent, or Firm*—Yong Zhao; Valerie J. Camaro

(57) ABSTRACT

This invention concerns compositions for the treatment of urinary frequency, urinary urgency and urinary incontinence comprising (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide Compound X

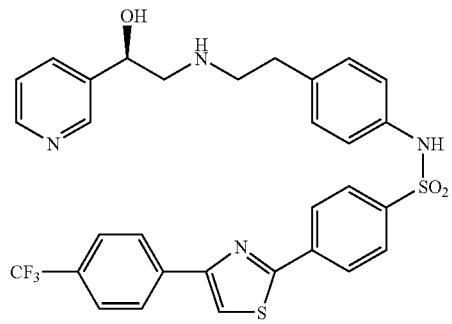

and pharmaceutically acceptable salts thereof. In another aspect, this invention concerns combination therapy for urinary frequency, urinary urgency and urinary incontinence wherein one of the active agents is (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide and pharmaceutically acceptable salts thereof.

2 Claims, No Drawings

COMBINATION THERAPY FOR THE TREATMENT OF URINARY FREQUENCY, URINARY URGENCY AND URINARY INCONTINENCE

CROSS REFERENCE TO RELATED APPLICATIONS

This application is a U.S. National Phase application under 35 U.S.C. §371 of PCT Application No. PCT/US2006/038419, filed Sep. 29, 2006 which claims priority under 35 U.S.C. §119(e) from U.S. Provisional Application Ser. No. 60/779,144, filed Mar. 3, 2006 and from U.S. Provisional Application Ser. No. 60/723,547, filed Oct. 4, 2005.

FIELD OF THE INVENTION

This invention concerns compositions for the treatment of urinary frequency, urinary urgency and urinary incontinence comprising (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide (compound X)

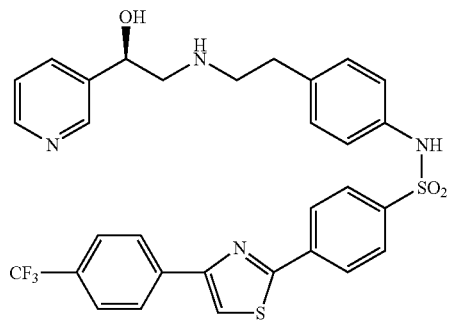

Compound X and pharmaceutically acceptable salts thereof. This invention concerns combination therapy for urinary frequency, urinary urgency and urinary incontinence wherein one of the active agents is (R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide. Compound X is a β3 adrenergic receptor (β3AR) agonist.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

The presence of β adrenergic receptors (βAR) in detrusor smooth muscle of various species, including human, rat, guinea pig, rabbit, ferret, dog, cat, pig and non-human primate has been evaluated using radioligand binding and/or functional studies in vitro. The latter typically involve measurement of relaxation in strips of bladder tissue pre-contracted using muscarinic agonists, endothelin agonists or KCl. Both approaches are complicated by the species differences among β3AR which impact the potency and pharmacological specificity of putative agonists and antagonists used to characterize β3AR. Nevertheless, in aggregate such pharmacological studies indicate there are marked species differences in the receptor subtypes mediating relaxation of the isolated detrusor, where β1AR predominate in cats and guinea pig, β2AR predominate in rabbit, and β3AR contribute or predominate in dog, rat, ferret, pig, cynomolgus and human detrusors. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97% cf 1.5% for β1AR mRNA and 1.4% for β2AR mRNA). Moreover, β3AR mRNA expression was equivalent in control and obstructed human bladders, as was relaxation evoked by the human β3AR agonist L-755507 in vitro. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Urinary frequency, urinary urgency is a disorder characterized by frequent and generally inappropriate strong urges to urinate. From a pathophysiologic point of view, urinary frequency, urinary urgency is most often associated with detrusor instability ("overactive bladder"), which may be intrinsic or may occur secondary to neurological conditions such as stroke or spinal cord injury. Urinary frequency, urinary urgency affects approximately 16% of both men and women; particularly in women, urinary frequency, urinary urgency often is accompanied by urinary incontinence, which is defined as socially inappropriate, involuntary loss of urine. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). See Ouslander J G. Management of Overactive Bladder. N Engl J Med 2004; 350:786-99. Therefore, there is need for new, well-tolerated therapies that effectively treat urinary frequency, urinary urgency and incontinence, either as monotherapy or in combination with available therapies.

β3AR are the most prevalent βAR subtype expressed on human detrusor smooth muscle. See Takeda H, Yamazaki Y, Akahane M, Akahane S, Miyata H, Igawa Y, Nishizawa O. Characterization of β-Adrenoceptor Subtype in Bladder Smooth Muscle in Cynomolgus Monkey, Jap J. Pharmacol 2002; 88:108-13. Like other βAR subtypes (i.e., β1AR, β2AR), agonist-promoted stimulation of membrane-bound β3AR results in increased intracellular levels of cyclic adenosine monophosphate (cAMP) via activation of G proteins and adenylyl cyclase. In isolated human bladder smooth muscle, activation of β3AR using subtype-selective agonists results in smooth muscle relaxation. Anticholinergics, which are the current mainstay of treatment for urinary frequency, urinary urgency and incontinence, also cause smooth muscle relaxation via inhibition of acetylcholine-promoted smooth muscle contraction. Thus, it is reasonable to hypothesize that other agents that relax bladder smooth muscle, such as β3AR agonists, may be effective for treating urinary urgency.

β2AR are also expressed on human detrusor, and clenbuterol, a β2AR-selective agonist, has been approved for the treatment of urinary frequency, urinary urgency in Japan. However, β2AR agonists are associated with significant mechanism-based side effects such as tachycardia due to stimulation of cardiac β2AR. Thus, use of β3AR-selective agonists may offer a therapeutic advantage by promoting selective detrusor relaxation while minimizing significant mechanism-based side effects such as those associated with anticholinergics or β2AR agonists.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume. In experimental models in rats detrusor instability can be evoked by outlet obstruction, with consequent bladder hypertrophy and spontaneous bladder contractions. Bladder hyperreflexia can be evoked by intravesicular instillation of acetic acid, PGE2 or other stimuli which activate sensory afferent fibers with attendant reduced voiding interval and spontaneous bladder contractions during filling. Hyperreflexia may also be induced by cerebral infarction (middle cerebral artery occlusion), the effects of which are attributed to decreased inhibitory supraspontine control. In the hyperreflexia paradigms, CL316243 administered intravenously dose-dependently normalizes voiding interval and produces decreases in voiding amplitude and increases in bladder capacity and compliance. In the detrusor instability paradigm CL316243 administered orally results in dose-dependent inhibition of spontaneous bladder contractions. See Takeda H, Yamazaki Y, Akahane M, Igawa Y, Ajisawa Y, Nishizawa O. Role of the β3-Adrenoceptor in Urine Storage in the Rat: Comparison Between the Selective β3-Adrenoceptor Agonist, CL316, 243, and Various Smooth Muscle Relaxants. J Pharm Exp Ther 2000; 293:939-45. See Woods M, Carson N, Norton N, Wesley S, Jeffery H, Argentieri T M. Efficacy of the [Beta]3-Adrenergic Receptor Agonist CL-316243 on Experimental Bladder Hyperreflexia and Detrusor Instability in the Rat. J Urol 2001, 166:1142-7. See Takeda H, Yamazaki Y, Igawa Y, Kaidoh K, Akahane S, Miyata H, Nishizawa O, Akahane M, Andersson K E. Effects of β3-Adrenoceptor Stimulation on Prostaglandin E2-Induced Bladder Hyperactivity and on the Cardiovascular System in Conscious Rats. Neurology and Urodynamics 2002; 21:558-65. Kaidoh K, Igawa Y, Takeda H, Yamazaki Y, Akahane S, Miyata H, Ajisawa Y, Nishizawa O, Andersson K E. Effects of Selective [beta]2 and [beta]3-Adrenoceptor Agonists on Detrusor Hyperreflexia in Conscious Cerebral Infarcted Rats. J Urol 2002; 168:1247-52.

Adequate sensory input is a prerequisite for normal bladder control and changes in sensory mechanisms may give rise to disturbances in bladder function. Thus, it has been proposed that urge incontinence is "a disease of bladder sensors". See Klein, L. A.: Urge incontinence can be a disease of bladder sensors. J Urol., 139: 1010-10-14, 1998. In spinal health, afferent activity from the bladder is mediated largely by the myelinated Aδ-fibers that pass through the spinal tracts to the brainstem and then to the pontine micturition center. After spinal disruption, a different type of afferent pathway emerges that is mediated by unmyelinated C-fibers that are sensitive to capsaicin. It is thought that these primary afferent C-fibers drive the spinal segmental reflex pathway and may be involved in pathological conditions of the bladder including overactivity and incontinence.

A renewed interest in tachykinins (TK) and especially NK receptor antagonists, on the micturition reflex is due to the recent introduction of C-fiber neurotoxins (capsaicin and res-inferatoxin) in urology for the treatment of both idiopathic micturition disorders and those related to neurological dysfunctions such as multiple sclerosis, Parkinson's disease and spinal cord injuries. See Maggi, C. A., Barbanti, G., Santicioli, P., Beneforti, P., Misuri, D., Meli, A. and Turini, D.: Cystometric evidence that capsaicin-sensitive nerves modulate the afferent branch of micturition reflex of humans. J. Urol., 142: 150, 1989. Lazzeri, M., Beneforti, P., Spinelli, M., Barbagli G., Turini D. Intravesical resiniferatoxin for the treatment of hypersensitive disorders: a randomized placebo controlled study. J Urol., 164:676-679, 2000. Dasgupta, P. and Fowler, C. J. Chilies from antiquity to urology. Brit. J. Urol., 80:845, 1997. Lecci A., birder, L., Meini, S., Giuliani, S., Tramontana, M., Criscuoli, M. Capsaicin and the micturition reflex: actions of tachykinins and other transmitters. Curr. Top. Pharmacol., 4; 193-220., 1998. M. B. Chancellor and W. C. de Groat, Intravesical capsaicin and resiniferatoxin therapy; spicing up the ways to treat the overactive bladder. J. Urol. 162; 3-11, 1999. Capsaicin, instilled directly into the bladder, was the first such agent used and it has been reported to achieve beneficial effects (i.e. increased bladder capacity) in ~70% of patients. Resiniferatoxin, which is ~100-fold more potent than capsaicin, causes prolonged inactivation of C-fibers without the initial stimulatory effects. See Avelino, A., Cruz, F., Coimbra, A. Intravesical resiniferatoxin desensitizes rat bladder sensory fibers without causing intense noxious excitation. A C-fos study. Eur J. Pharmacol., 378; 17-25, 1999. The introduction of these agents into humans was supported by several animal studies that showed local or systemic treatment with capsaicin or resiniferatoxin, at doses that depleted substance P and neurokinin A in the bladder, caused an increase in bladder capacity and reduced bladder hyperactivity. See Holzer-Petsche, U. and Lembeck, F. Systemic capsaicin treatment impairs the micturition reflex in the rat. Br. J. Pharmacol. 83; 935-941, 1984. Cheng, C. I., Ma, C. P. and de Groat, W. C. Effect of capsaicin on micturition and associated reflexes in rats. Amer. J. Physiol., part 2, 34; R132, 1993. Cheng, C. I., Ma, C. P. and de Groat, W. Effect of capsaicin on micturition and associated reflexes in chronic spinal rats. Brain Res., 678; 40-48, 1995. Maggi, C. A., Santicioli, P. and Meli, A.: The effects of topical capsaicin on rat urinary bladder motility in vivo. Eur. J. Pharmacol., 103; 41-51, 1984. Santicioli, P., Maggi, C. A. and Meli, A.: The effect capsaicin pretreatment on the cystometrograms of urethane anesthetized rats. J. Urol., 133; 700-708, 1985. Thus, a possible role of tachykinins as sensory transmitters in the micturition reflex has been postulated and $NK_1$ and/or $NK_2$ receptor antagonists may induce the same effects as capsaicin by inhibiting the sensorial input from the bladder to the spinal cord, thus increasing the threshold to initiate micturition.

The effects of selective $NK_1$ and $NK_2$ receptor antagonists have been studied in various animal models of bladder function. Using a cyclophosphamide-induced model of bladder overactivity, it has been shown that two $NK_1$ antagonists (GR 82334 and RP 67580) increased the volume threshold after i.t., but not i.v. administration. A moderate response in this model was also observed with the $NK_2$ antagonist SR 48968 (10 nmol/rat), however the i.v. co-administration of $NK_1$ and NK$_2$, antagonists did not modify urodynamic variables in either vehicle- or cyclophosphamide-treated rats. See Lecci, A., Giuliani, S., Santicioli, P., Maggi, C. A. Involvement of spinal tachykinin NK1 and NK2 receptors in detrusor hyper-reflexia during chemical cystitis in anaesthetized rats. Eur J. Pharmacol., 259; 129-135, 1994. Using RP 67580 and SR 48968, Ishizuka et al., found that spinal NK$_1$ receptors are involved in the micturition reflex induced by bladder filling in animals with bladder hypertrophy secondary to outflow obstruction. See Ishizuka, O., Igwana, Y., Lecci, A., et al. 1994. Role of intrathecal tachykinin for micturition in unanesthetized rats with and without bladder outlet obstruction. Br. J. Pharmacol. 113, 111-123. Another study determined that intrathecal administration of GR 82334 blocked capsaicin-induced micturition reflex in rats. Importantly, at the same doses proved effective in the chemonociceptive reflex, GR 82334 did not affect the micturition reflex induced by bladder filling or the force of contraction induced by perineal pinching. See Lecci, A., Giuliani, S., Maggi, C. A. Effect of the NK-1 receptor antagonist GR 82334 on reflexly-induced bladder contractions. Life Sciences, 51; 277-280, 1992.

Scientists at Takeda Laboratories have investigated the effects of TAK-637 on lower urinary tract function in guinea pigs and cats. Kamo and Doi, reported that in decerebrate cats, TAK-637 (0.1, 0.3, 1 and 3 mg/kg i.v.) produced a dose-dependent increase in bladder capacity (maximal increase was 94%) without any significant reduction in voiding efficiency. TAK-637 at 3 mg/kg i.v. did not inhibit the micturition reflex induced by electrical stimulation of the rostral brainstem near the locus coeruleus, indicating that it does not impair the efferent pathways of the micturition reflex. These results suggest that TAK-637 increases bladder storage capability without inhibiting the voiding function of the lower urinary tract, presumably by inhibiting the afferent pathway of the micturition reflex rather than the efferent pathway. The systemic administration of TAK-637 decreased the number but not the amplitude of distension-induced rhythmic bladder contractions in guinea pig, an effect which was also observed in animals with severed spinal cords. TAK-637 also inhibited the micturition reflex induced by topical application of capsaicin (which stimulates primary afferent nerve endings in the bladder wall) onto the surface of the bladder dome. These results suggest that TAK-637 inhibits sensory transmission from the bladder evoked by both physiological and nociceptive stimuli by blocking tachykinin NK$_1$ receptors, almost certainly at the level of the spinal cord. Furthermore, TAK-637 inhibits the spinal vesico-vesical reflex induced by electrical stimulation of the proximal cut end of the pelvic nerve in spinal animals, but not bladder contractions induced by electrical stimulation of the distal cut end of the nerve. Tissue bath studies showed that TAK-637 had no effect on carbachol or electrical field stimulation induced contractions of isolated bladder strips, whereas other drugs used for abnormally frequent micturition inhibited both contractions. These results suggest that TAK-637 inhibits the micturition reflex by acting, at least in part, on NK$_1$ receptors in the spinal cord, a mechanism of action clearly different from antimuscarinics or spasmolytics NK-1 receptor antagonists, and in particular, those whose use is claimed herein, are also believed to be useful in the treatment of Lower Urinary Tract Symptoms (LUTS).

See Moller, et. al., BMJ 2000; 320: 1429-1432 (27 May); Pinnock and Marshall, MJA 1997; 167: 72-75 (21 July); Moller, et. al., Obstetrics & Gynecology 2000; 96:446-451; and Clinical Practice Guidelines: The Management of Uncomplicated Lower Urinary Tract Symptoms in Men, UHMRC 2000.

SUMMARY OF THE INVENTION

In one aspect, this invention concerns a pharmaceutical composition for the treatment of urinary frequency, urinary urgency and urinary incontinence comprising a therapeutically effective amount of (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide (compound X)

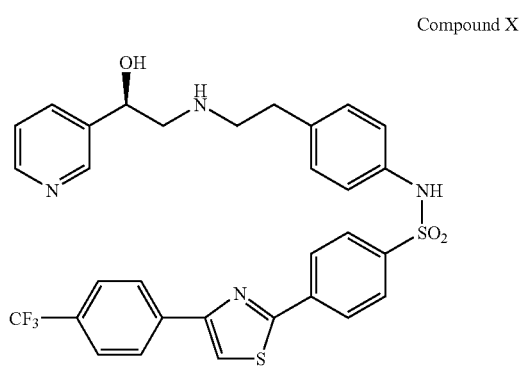

Compound X and pharmaceutically acceptable salts thereof.

In another aspect, this invention concerns combination therapy and pharmaceutical compositions the treatment of urinary frequency, urinary urgency and urinary incontinence wherein one of the active agents is (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide and pharmaceutically acceptable salts thereof.

DETAILED DESCRIPTION OF THE INVENTION

In one aspect, this invention concerns a pharmaceutical composition for the treatment of a disease selected from urinary frequency, urinary urgency or urinary incontinence comprising a therapeutically effect amount of (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide

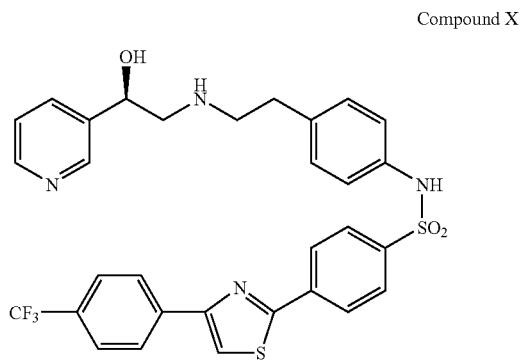

Compound X or pharmaceutically acceptable salt thereof and a pharmaceutically acceptable carrier.

Within this aspect, there is a genus comprising (R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide or a salt thereof and a therapeutically effective amount of at least one additional active agent, wherein the additional active agent is selected from the group consisting of (a) an antagonist of the NK-1 receptor selected from:

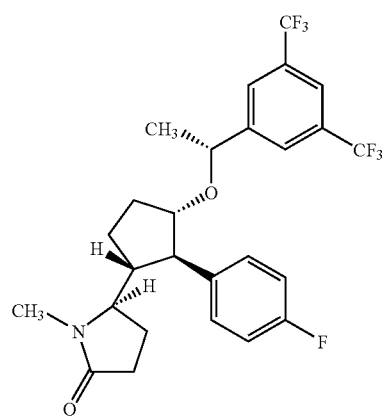

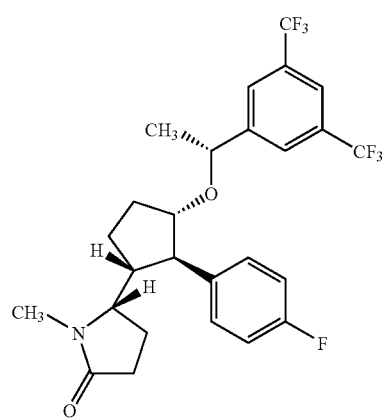

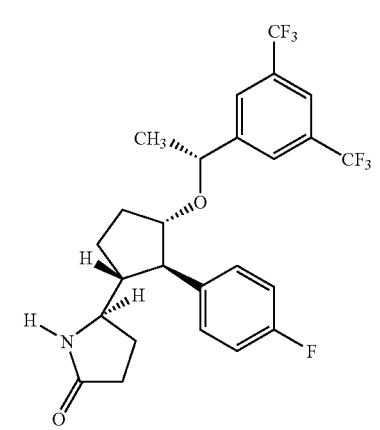

-continued

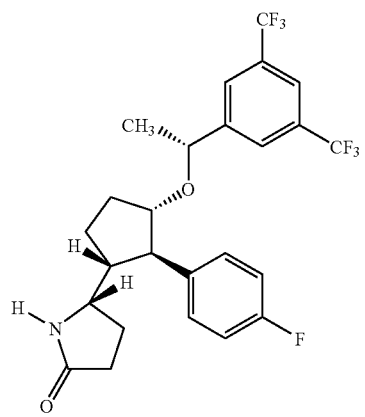

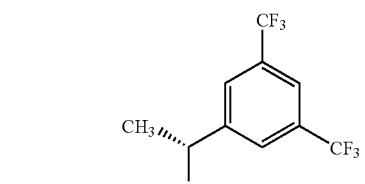

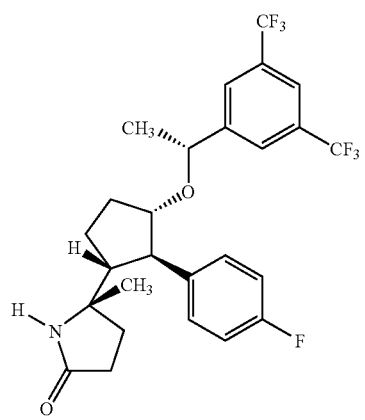

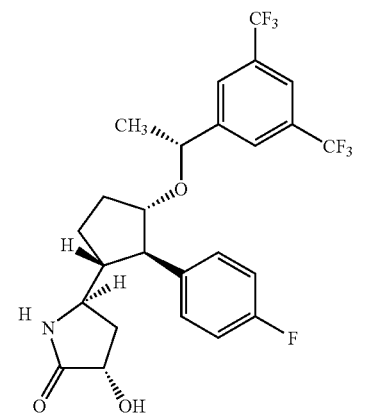

-continued
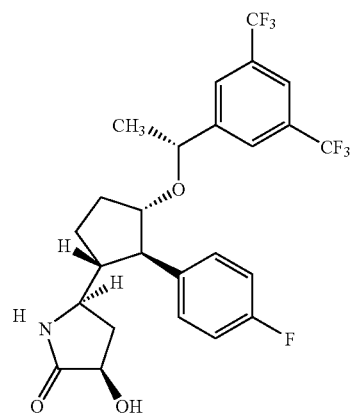
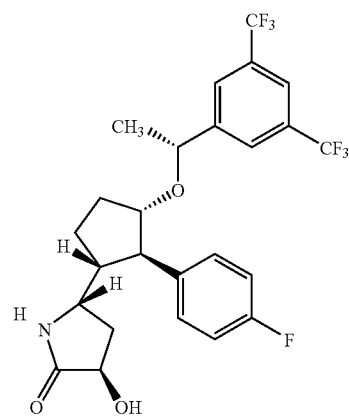
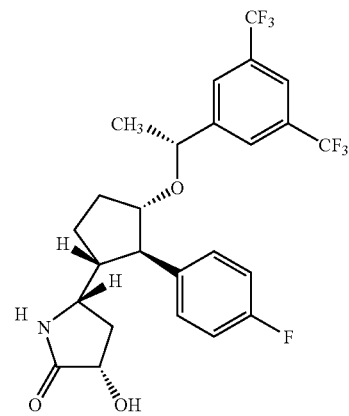
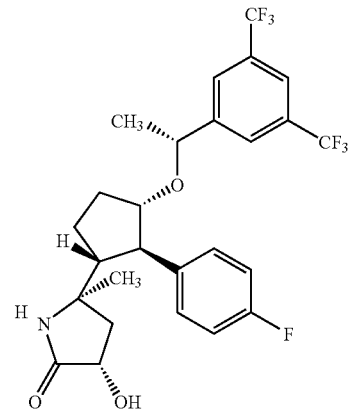
-continued
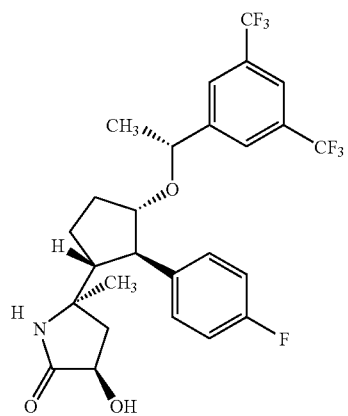
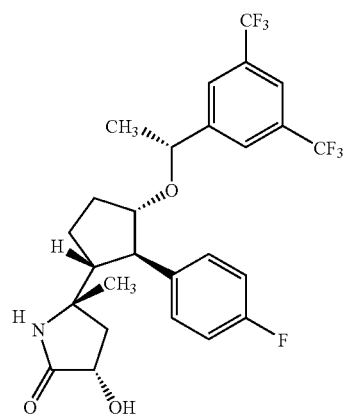
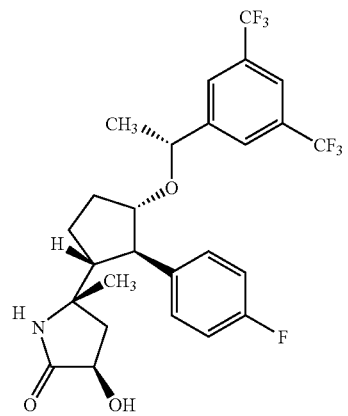
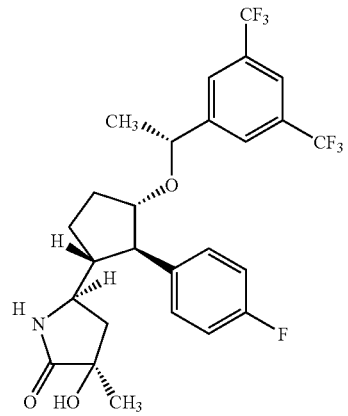

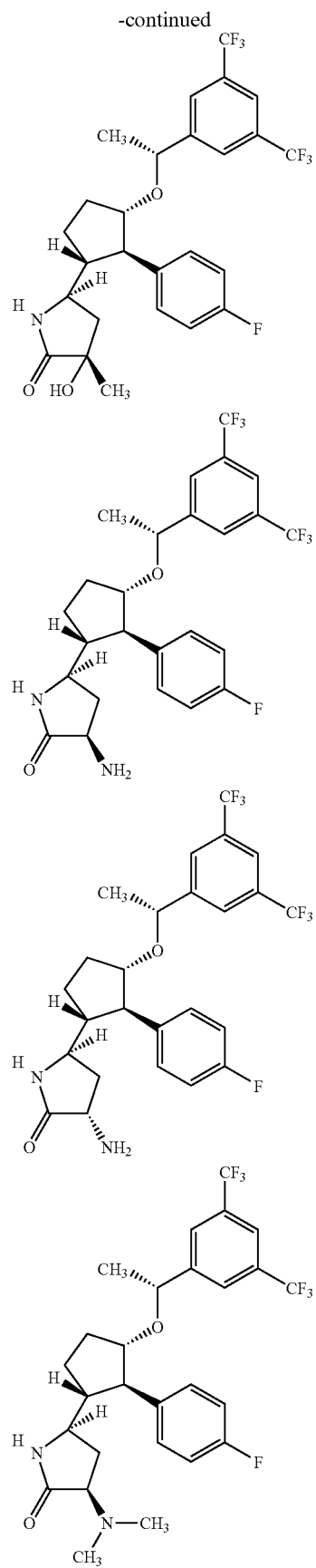
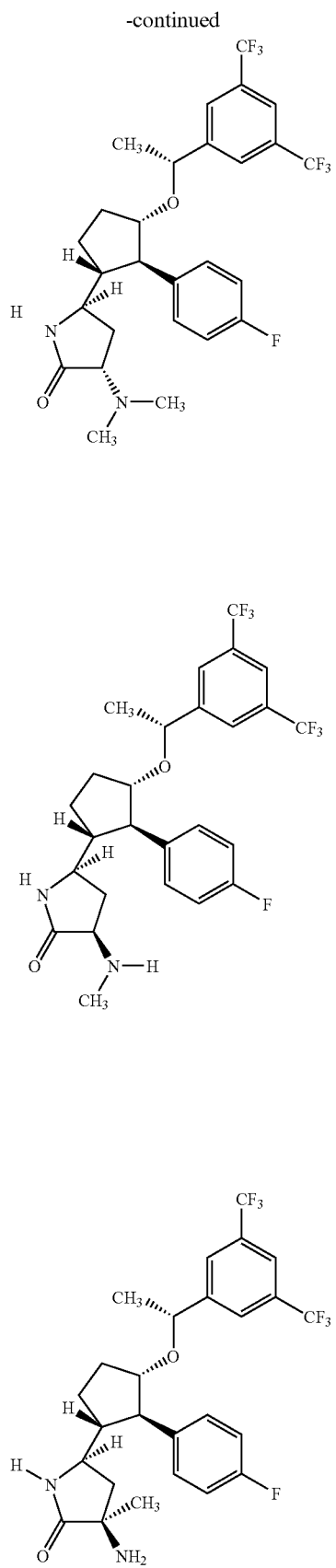

-continued
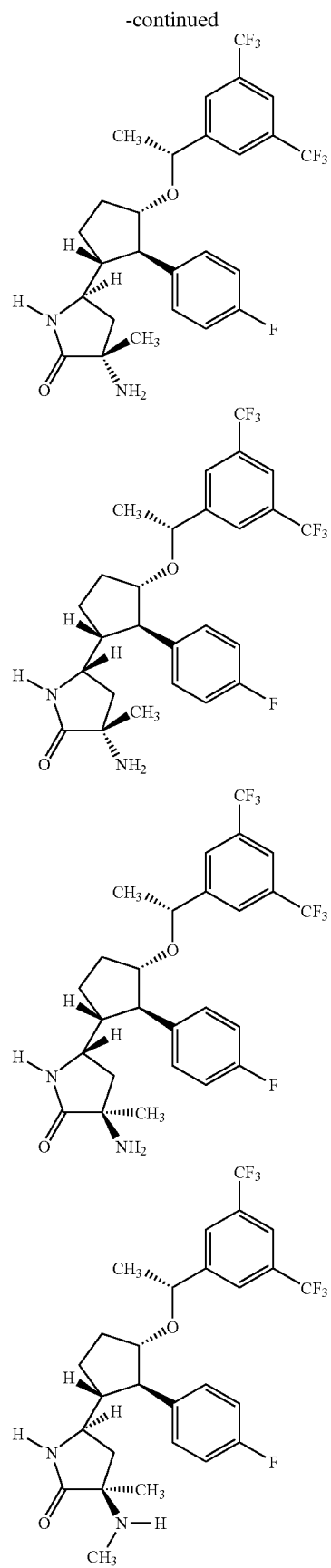
-continued
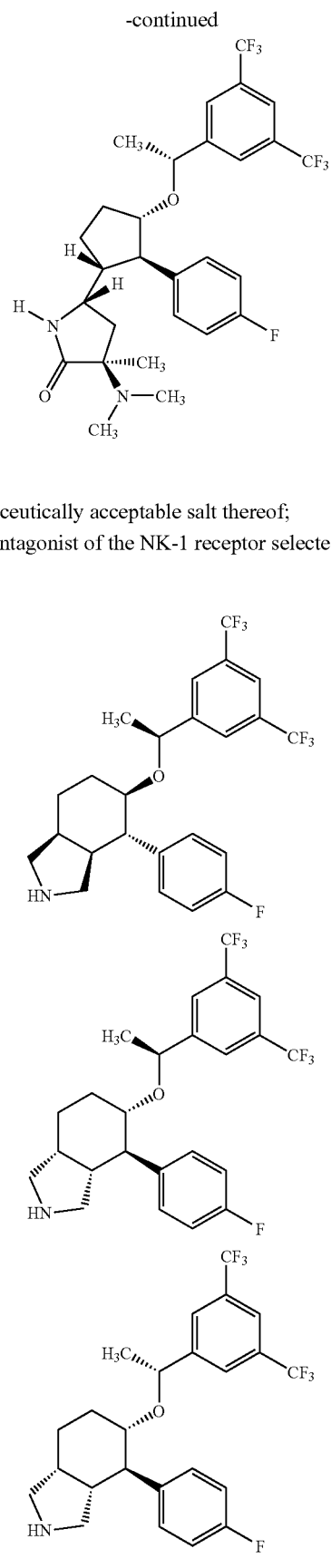
or pharmaceutically acceptable salt thereof;
(b) an antagonist of the NK-1 receptor selected from

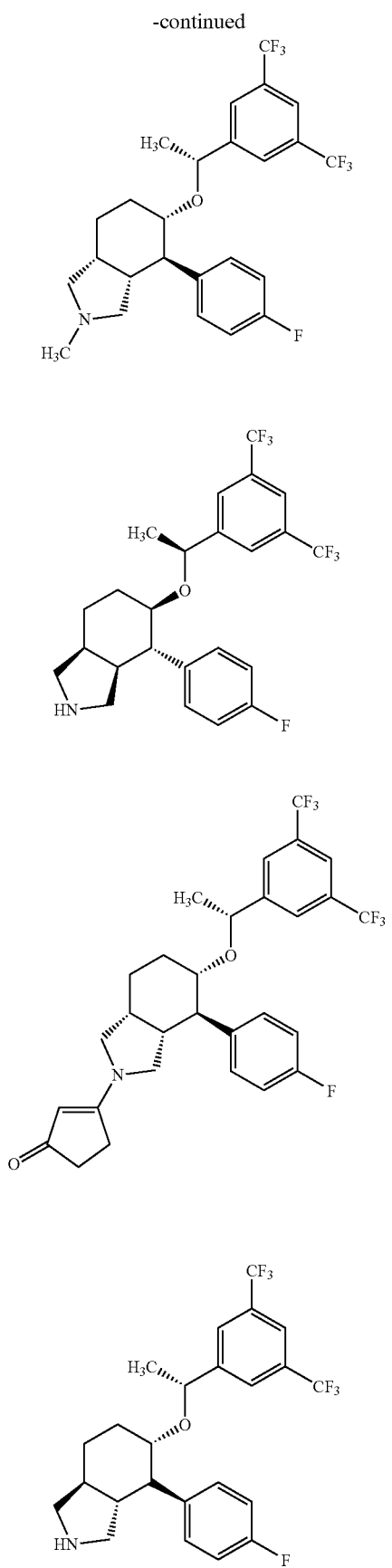
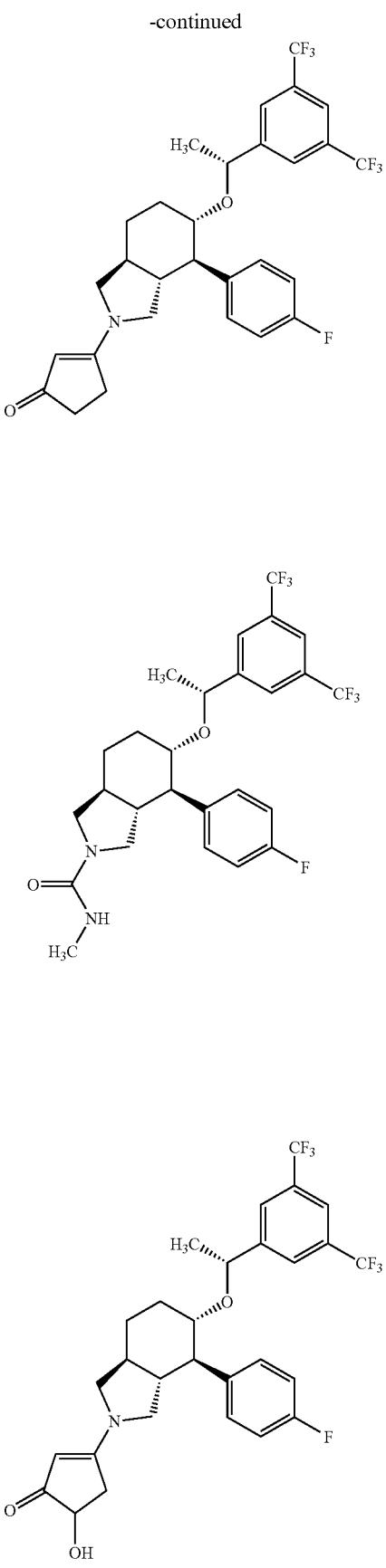

-continued
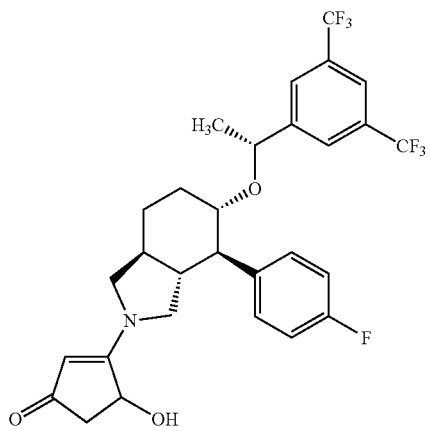
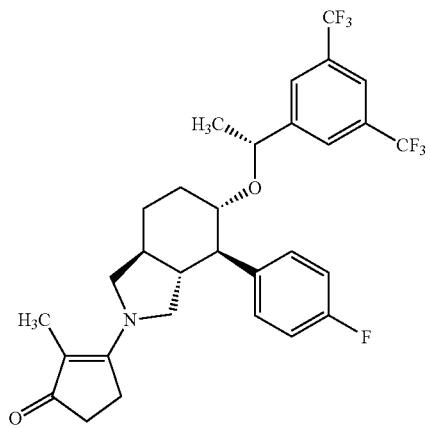
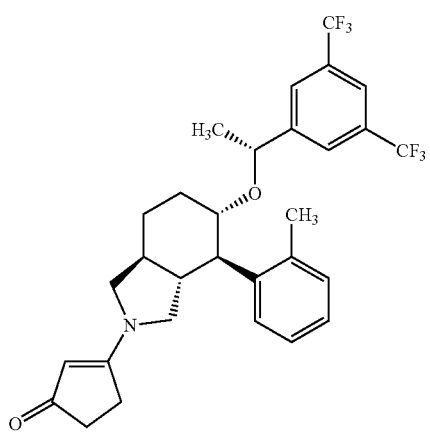
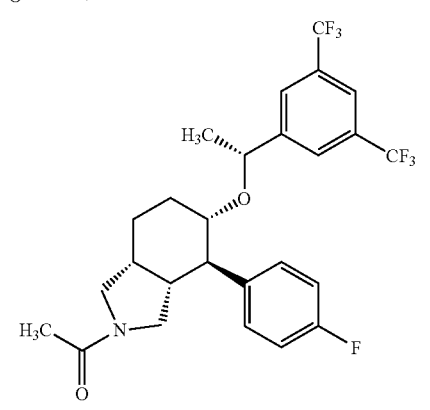
-continued
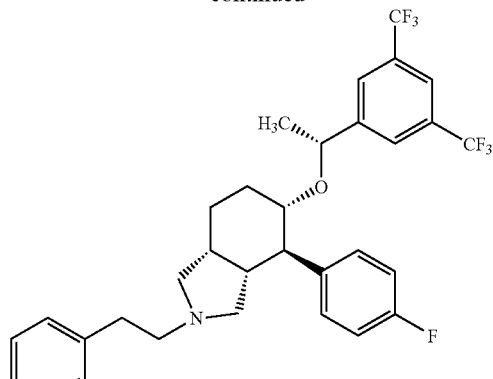
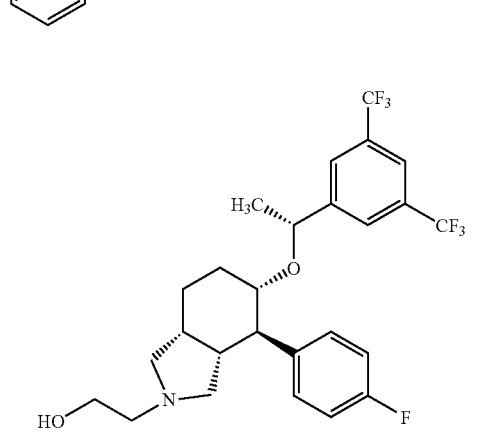
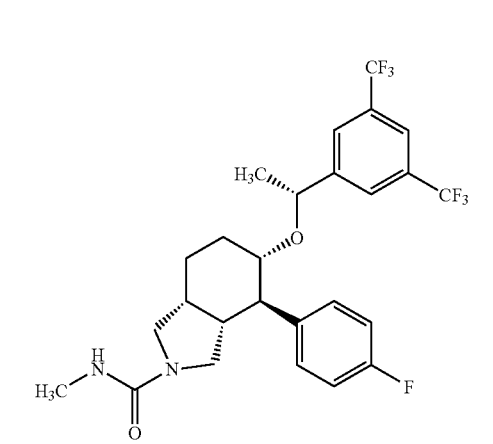
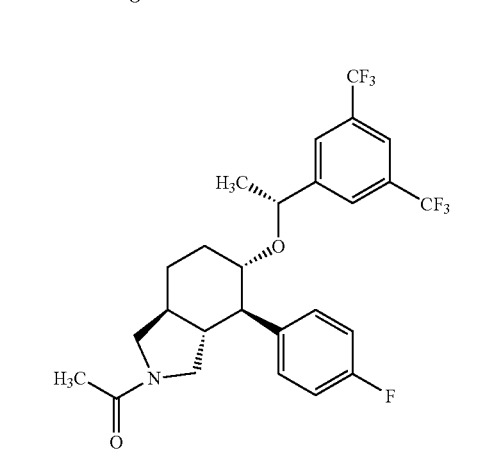

-continued
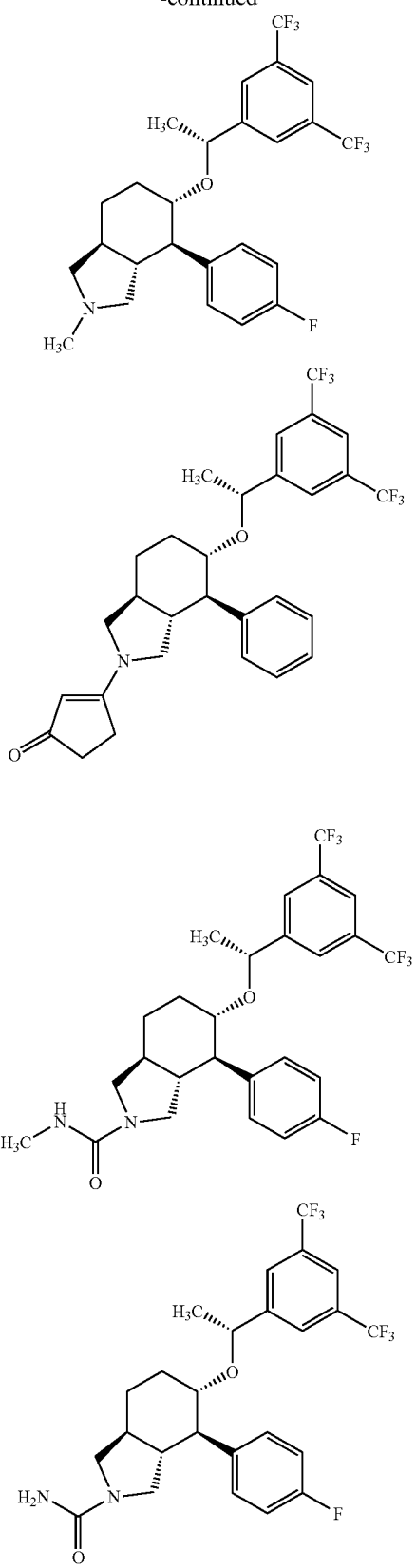
or pharmaceutically acceptable salt thereof;
(c) an NK-1 receptor antagonist of the formula
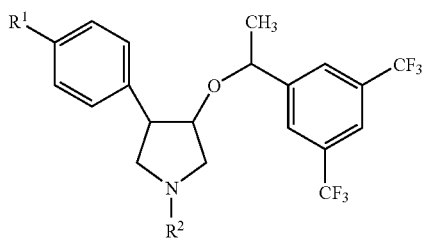
wherein $R^2$ and $R^1$ are selected from the table below:
| $R^2$ | $R^1$ |
|---|---|
|  | F |
|  | H |
| 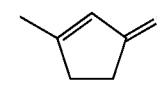 | F |
| 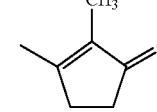 | F |
| 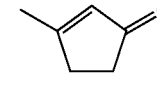 | H |
| 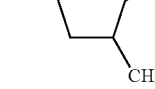 | F |
| 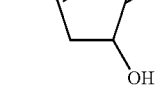 | F |
| 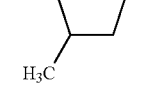 | F |
| 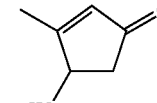 | F |

-continued
| R² | R¹ |
|---|---|
| 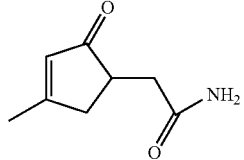 | F |
| 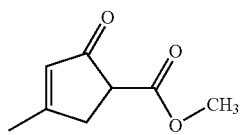 | F |
| 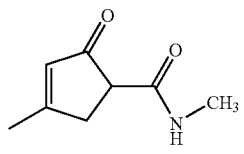 | F |
| 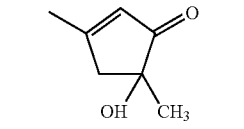 | F |
| H | F |
| 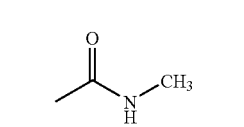 | F |
| 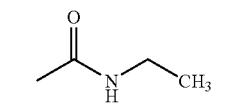 | F |
| 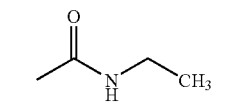 | H |
| 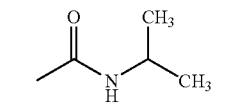 | F |
| 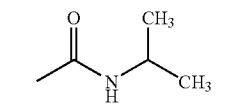 | H |
| 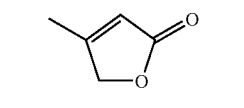 | F |
| 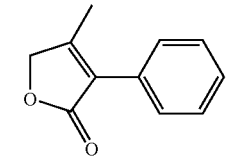 | F |
-continued
| R² | R¹ |
|---|---|
| 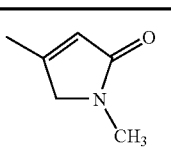 | F |
| 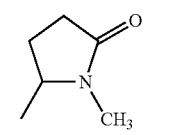 | F |
| 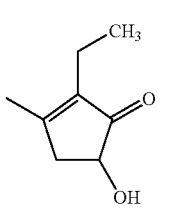 | F |
| 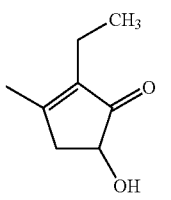 | F |
| 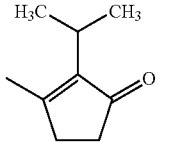 | F |
| 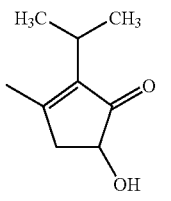 | F |
| 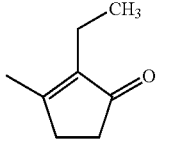 | F |
| 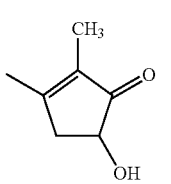 | F |

| R² | R¹ |
|---|---|
| 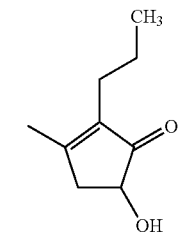 | F |
| 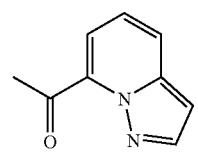 | F |
| 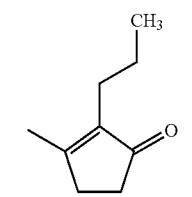 | F |
| 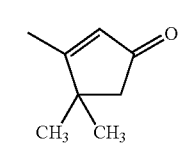 | F |
| 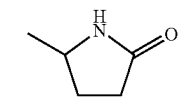 | F |
| 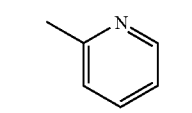 | F |
| 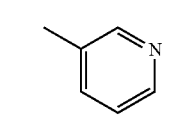 | F |
| 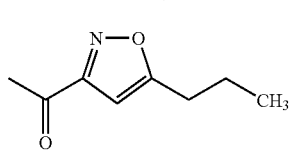 | F |
| 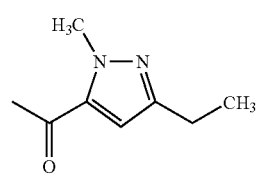 | F |
| 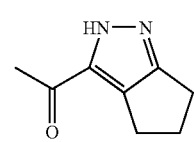 | F |
| R² | R¹ |
|---|---|
| 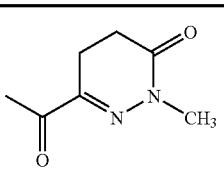 | F |
| 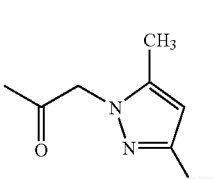 | F |
| 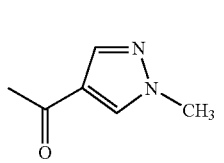 | F |
| 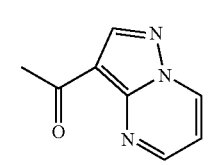 | F |
| 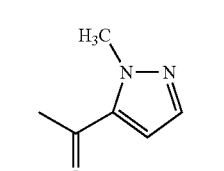 | F |
| 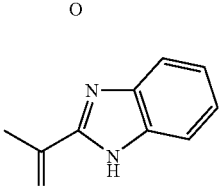 | F |
| 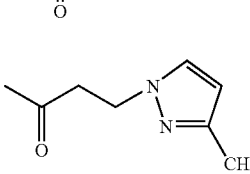 | F |
| 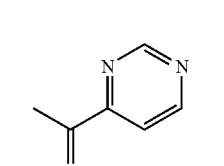 | F |
| 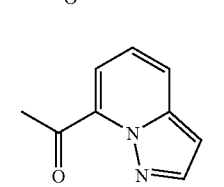 | F |

| R² | R¹ |
|---|---|
| 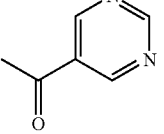 | F |
| 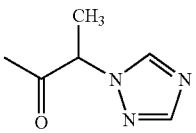 | F |
| 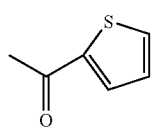 | F |
| 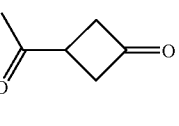 | F |
| 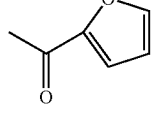 | F |
| 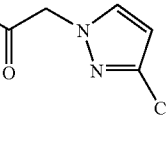 | F |
| 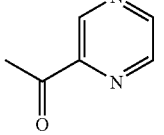 | F |
| 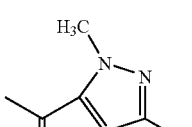 | F |
| 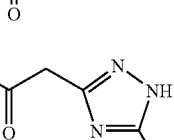 | F |
| 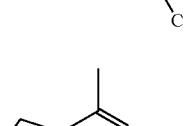 | H |

| R² | R¹ |
|---|---|
| 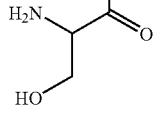 | H |
| 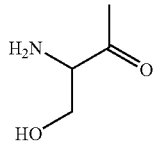 | F |
| 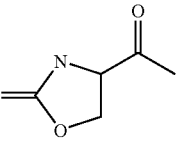 | H |
| 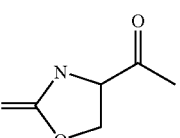 | F |
| 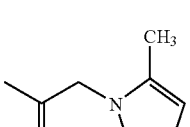 | F; | or pharmaceutically acceptable salts thereof.

(d) an NK-1 receptor antagonist selected from the group consisting of:

(3R,4S)-1-Acetyl-3-({(1R)-1-[3,5-bis(trifluoromethyl)phenyl]ethyl}oxy)-4-phenylpyrrolidine;

(3R,4S)-3-({((R)-1-[3,5-Bis(trifluoromethyl)phenyl]ethyl}oxy)-4-(4-fluorophenyl)-N-methylpyrrolidine-1-carboxamide;

3-[(3R,4S)-3-({(1R)-1-[3,5-Bis(trifluoromethyl)phenyl]ethyl}oxy)-4-(4-fluorophenyl)pyrrolidin-1-yl]cyclopent-2-en-1-one;

tert-Butyl 4-{[(3R,4S)-3-({(1R)-1-[3,5-bis(trifluoromethyl)phenyl]ethyl}oxy)-4-phenylpyrrolidin-1-yl]carbonyl}-2,2-dimethyl-1,3-oxazolidine-3-carboxylate;

2-Amino-3-[(3R,4S)-3-({(1R)-1-[3,5-bis(trifluoromethyl)phenyl]ethyl}oxy)-4-phenylpyrrolidin-1-yl]-3-oxopropan-1-ol;

4-{[(3R,4S)-3-({(1R)-1-[3,5-Bis(trifluoromethyl)phenyl]ethyl}oxy)-4-phenylpyrrolidin-1-yl]carbonyl}-1,3-oxazolidin-2-one;

3-[(3R,4R)-3-({(1R)-1-[3,5-Bis(trifluoromethyl)phenyl]ethyl}oxy)-4-(4-fluorophenyl)pyrrolidin-1-yl]cyclopent-2-en-1-one;

(5R)-3-[(3R,4S)-3-({(1R)-1-[3,5-Bis(trifluoromethyl)phenyl]ethyl}oxy)-4-(4-fluorophenyl)pyrrolidin-1-yl]-5-methylcyclopent-2-en-1-one;

(5S)-3-[(3R,4S)-3-({(1R)-1-[3,5-Bis(trifluoromethyl)phenyl]ethyl}oxy)-4-(4-fluorophenyl)pyrrolidin-1-yl]-5-methylcyclopent-2-en-1-one;

(5R)-3-[(3R,4S)-3-({(1R)-1-[3,5-Bis(trifluoromethyl)phenyl]ethyl}oxy)-4-(4-fluorophenyl)pyrrolidin-1-yl]-5-hydroxycyclopent-2-en-1-one;
(5S)-3-[(3R,4S)-3-({(1R)-1-[3,5-Bis(trifluoromethyl)phenyl]ethyl}oxy)-4-(4-fluorophenyl)pyrrolidin-1-yl]-5-hydroxycyclopent-2-en-1-one;
3-[(3R,4S)-3-({(1R)-1-[3,5-Bis(trifluoromethyl)phenyl]ethyl}oxy)-4-(4-fluorophenyl)pyrrolidin-1-yl]-4-methylcyclopent-2-en-1-one;
(4R)-3-[(3R,4S)-3-({(1R)-1-[3,5-Bis(trifluoromethyl)phenyl]ethyl}oxy)-4-(4-fluorophenyl)pyrrolidin-1-yl]-4-hydroxycyclopent-2-en-1-one;
2-{2-[(3R,4S)-3-({(1R)-1-[3,5-Bis(trifluoromethyl)phenyl]ethyl}oxy)-4-(4-fluorophenyl)pyrrolidin-1-yl]-5-oxocyclopent-1-en-1-yl}acetamide;
Methyl 2-[(3R,4S)-3-({(1R)-1-[3,5-bis(trifluoromethyl)phenyl]ethyl}oxy)-4-(4-fluorophenyl)pyrrolidin-1-yl]-5-oxocyclopent-1-ene-1-carboxylate; and
2-[(3R,4S)-3-({(1R)-1-[3,5-Bis(trifluoromethyl)phenyl]ethyl}oxy)-4-(4-fluorophenyl)pyrrolidin-1-yl]-N-methyl-5-oxocyclopent-1-ene-1-carboxamide; and
(e) an anti-muscarinic agent, such as tolterodine.

Within this genus there is a sub-genus wherein the NK-1 receptor antagonists are selected from group (a).

Within this sub-genus is a class wherein there are exactly two active agents:

(R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide or a salt thereof, and one NK-1 receptor antagonist selected from group (a).

Within this sub-genus is a class wherein there are exactly two active agents:

(R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide or a salt thereof, and the NK-1 receptor antagonist:

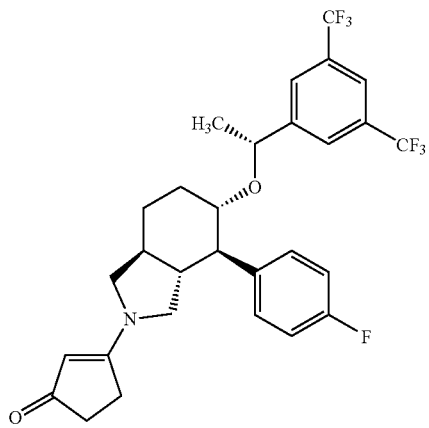

or a pharmaceutically acceptable salt thereof.

Within this genus there is a sub-genus wherein the NK-1 receptor antagonists are selected from group (b).

Within this sub-genus is a class wherein there are exactly two active agents:

(R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide or a salt thereof, and one NK-1 receptor antagonist selected from group (b).

Within this sub-genus is a class wherein there are exactly two active agents:

(R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide or a salt thereof, and the NK-1 receptor antagonist:

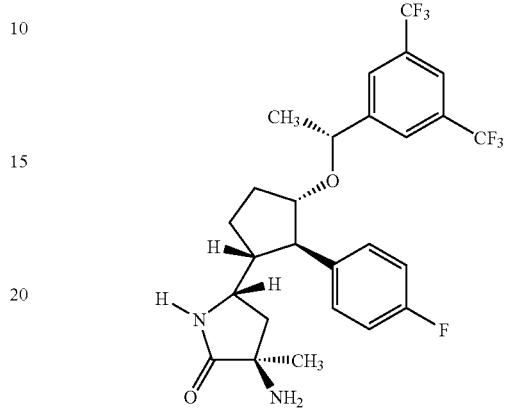

of a pharmaceutically acceptable salt thereof.

Within this genus there is a sub-genus wherein the NK-1 receptor antagonists are selected from group (c).

Within this sub-genus is a class wherein there are exactly two active agents:

(R)-N-[4-[2-[[2-Hydroxy-2-(pyridin-3-yl)ethyl]amino]ethyl]phenyl]-4-[4-(4-trifluoromethylphenyl)thiazol-2-yl]benzenesulfonamide or a salt thereof, and one NK-1 receptor antagonist selected from group (c).

Within this genus there is a sub-genus wherein the NK-1 receptor antagonists are selected from group (d).

Within this sub-genus is a class wherein there are exactly two active agents:

(R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide or a salt thereof, and one NK-1 receptor antagonist selected from group (d).

Within this genus is a sub-genus wherein there are exactly two active agents:

(R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide or a salt thereof, and tolterodine.

In another aspect this invention is directed to a method of treating a disease selected from urinary frequency, urinary urgency and urinary incontinence, comprising the administration of (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide or a salt thereof.

Within this aspect there is a genus comprising the administration of (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide or a salt thereof and at least one additional active agent selected from group (a), (b), (c), (d) and (e).

A number of compounds can be used in any of the aspects of invention as an alternative to tolterodine. These include: oxybutynin, trospium, vamicamide, solifenacin, propiverine, S-oxybutynin, temiverine, sanctura, staybla, fesoterodine, SVT40776, 202405 by GlaxoSmithKline, TD6301, RBX9841, DDP200, and PLD179. See, for example, U.S. Pat. Nos. 5,382,600; 3,176,019; 3,480,626; 4,564,621; 5,096, 890; 6,017,927; 6,174,896; 5,036,098; 5,932,607; 6,713,464; 6,858,650; and DD 106643. See also, U.S. Pat. Nos. 6,103, 747; 6,630,162; 6,770,295; 6,911,217; 5,164,190; 5,601,839; 5,834,010; 6,743,441; WO2002000652; WO200400414853. These also include trospium chloride, darifenacin and imidafenacin (KRP-197). As will be appreciate by those of skill in the art, these drugs may be administered orally or topically in standard or extended release forms, such as extended release tolterodine, extended release oxybutynin and transdermal oxybutynin.

Accordingly, in one aspect his invention concerns a pharmaceutical composition for the treatment of a disease selected from urinary frequency, urinary urgency or urinary incontinence comprising a therapeutically effect amount of (R)-N-[4-[2-[[2-hydroxy-2-(pyridin-3-yl)ethyl]amino] ethyl]phenyl]-4-[4-(4-trifluoromethylphenyl)thiazol-2-yl] benzenesulfonamide and a therapeutically effective amount of an anti-muscarinic agent selected from the group consisting of tolterodine, oxybutynin, trospium, vamicamide, solifenacin, propiverine, S-oxybutynin, temiverine, sanctura, staybla, fesoterodine, SVT40776, 202405 by GlaxoSmithKline, TD6301, RBX9841, DDP200, and PLD 179.

Accordingly, in one aspect his invention concerns a pharmaceutical composition for the treatment of a disease selected from urinary frequency, urinary urgency or urinary incontinence comprising a therapeutically effect amount of (R)-N-[4-[2-[[2-hydroxy-2-(pyridin-3-yl)ethyl]amino] ethyl]phenyl]-4-[4-(4-trifluoromethylphenyl)thiazol-2-yl] benzenesulfonamide and a therapeutically effective amount of an anti-muscarinic agent selected from the group consisting of include trospium chloride, darifenacin and imidafenacin.

In one aspect his invention concerns a pharmaceutical composition for the treatment of a disease selected from urinary frequency, urinary urgency or urinary incontinence comprising a therapeutically effect amount of (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide and a therapeutically effective amount of an anti-muscarinic agent selected from the group consisting of extended release tolterodine, extended release oxybutynin and transdermal oxybutynin.

In one aspect his invention concerns a pharmaceutical composition for the treatment of a disease selected from urinary frequency, urinary urgency or urinary incontinence comprising a therapeutically effect amount of (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide and a therapeutically effective amount of an anti-muscarinic agent selected from the group consisting of darifenacin or oxybutynin, wherein the oxybutynin includes extended release oxybutynin and transdermal oxybutynin.

Pharmaceutical compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleageneous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The compositions containing compounds of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms. The compositions containing compounds of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories. The term "therapeutically effective amount" refers to a sufficient quantity of the compounds of the present invention, in a suitable composition, and in a suitable dosage form to treat or prevent the noted disease conditions.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds. By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (humans and animals, including companion animals, such as dogs, cats and horses) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

A suitable dosage level of Compound X of the present invention, or pharmaceutically acceptable salts thereof, is about 25 to 750 mg per day, which may be given as a single dose or divided into two or three doses per day. Preferably, the dosage range will be about 50.0 mg to 375 mg per patient per day; more preferably about 50.0 to 250 or 100 to 375.0 mg per patient per day. Specific dosages of the compounds of the present invention, or pharmaceutically acceptable salts thereof, for administration include 1 mg, 25 mg, 50 mg, 100 mg, 125 mg, 200 mg, 250 mg, and 375 mg.

A suitable dosage level of the NK-1 receptor antagonist or pharmaceutically acceptable salts thereof, is about 0.001 to 50 mg/kg per day, in particular about 0.01 to about 25 mg/kg, such as from about 0.05 to about 10 mg/kg per day. The dosage range will generally be about 0.5 to 1000 mg per patient per day, which may be administered in single or multiple doses. Preferably, the dosage range will be about 0.5 mg to 500 mg per patient per day; more preferably about 0.5 mg to 200 mg per patient per day; and even more preferably about 1 mg to 10 mg or 5 mg to 50 mg per patient per day. Specific dosages of the compounds of the present invention, or pharmaceutically acceptable salts thereof, for administration include 1 mg, 5 mg, 10 mg, 30 mg, 100 mg, and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 10 or 100 mg active ingredient. Specific pharmaceutical compositions comprise about 1 mg, 5 mg, 10 mg, 30 mg, 100 mg, and 500 mg of active ingredient.

A suitable dosage level of tolterodine includes that presently approved for the drug, such a 1, 2 or 4 mg of tolterodine tartrate, once or twice a day.

(R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide, and methods of making same are disclosed in WO98/32753, published Jul. 30, 1998.

The NK-1 receptor antagonists of group (a) and methods of making same are disclosed in the Examples section, herein under.

The NK-1 receptor antagonists of group (b) and methods for making same are disclosed in WP2005/073191, published Aug. 11, 2005.

The NK-1 receptor antagonists of group (c) and (d) and methods of making same are disclosed in the WO2005/032464, published Apr. 14, 2005.

Tolterodine ((R)-N,N-diisopropyl-3-(2-hydroxy-5-methylphernyl)-3-propanamine) and methods of making same are disclosed in U.S. Pat. No. 5,382,600.

Intermediate 1

((1R),(2R),(3S))-3-((1R)-1-(3,5-bis(Trifluoromethyl)phenyl)ethoxy)-2-(4-fluorophenyl)cyclopentane-carboxylic acid Method A: The title compound was prepared as described in U.S. Pat. No. 5,750,549 or was obtained from its ½ TEA salt as described in U.S. Pat. No. 6,479,518 and J. Org. Chem., 67, 5993-6000 (2002). In the latter case, the ½ TEA salt was suspended in water, the water was acidified with 2N HCl until the pH was less than 2, and the mixture was extracted twice with ethyl acetate. The ethyl acetate layers were each successively washed with brine, combined, and dried over sodium sulfate. Removal of solvent in vacuo afforded the free acid as a thick oil which solidified on standing.

Method B: The title compound was also prepared as follows. To a 100 L flask was charged sequentially 113.3 g (0.50 mol) of Pd(OAc)$_2$, 331.4 g (1.11 mol) of 2-(di-t-butylphosphino)biphenyl, 2.476 kg (25.24 mol) of 1, 3-cyclopentanedione, and 10.72 kg (50.5 mol) of powdered K$_3$PO$_4$. The resulting mixture was degassed (3×) by vacuum/N$_2$ back fills. The vessel was then charged with 26 L of 1, 4-dioxane and 4.28 kg (32.78 mol) of 1-chloro-4-fluorbenzene and the vessel degassed (3×) with vacuum/N$_2$ back fills. The resulting slurry was heated to reflux for 12 h, cooled to rt, and water (23 L) was added. The vessel was rinsed with an additional 6 L of water and the reaction mixture further diluted with an additional 46 L of water. To the homogeneous solution was added 9 L of conc. HCl to adjust the pH to 1 and the solution aged for 2.5 h. The slurry was then filtered and the cake washed with 17 L of water and 17 L of toluene. The solid was then dried at 60° C. for 48 h, providing 2-(4-fluoro-phenyl)-1,3-cyclopentanedione as a light tan solid.

To a solution of 30.8 mL of THF in a stirred autoclave was added sequentially 17.31 g (81.54 mmol) of K$_3$PO$_4$, 4.0 g (40.8 mmol) of 1, 3-cyclopentanedione, 268 mg (0.989 mmol) of 2-(di-t-butylphosphino)biphenyl, 91.5 mg (0.405 mmol) of Pd(OAc)$_2$, and 6.92 g (53.0 mmol) of 1-chloro-4-fluorobenzene. The sides of the reaction vessel were washed with an additional 10 mL of THF and the vessel purged 3 times with vacuum and nitrogen. The heterogeneous reaction mixture was then heated to 100° C., generating 25 psig pressure in the vessel. The reaction was aged at 100° C. for 12 h, cooled to rt, and diluted with 150 mL of water. The resulting homogeneous mixture was distilled to remove THF and then heated to 50° C. The aqueous solution was then slowly acidified using conc. HCl until a final pH of 3 was obtained (10.6 mL). The slurry was cooled to rt and filtered. The wet cake was washed with 40 mL of water, 40 mL of toluene, and dried under vacuum at 60° C. for 24 h to give 2-(4-fluorophenyl)-1,3-cyclopentanedione as a light brown solid.

To a 1-Liter 3-neck flask was charged 50 g (0.26 mol) of 2-(4-fluorophenyl)-1,3-cyclopentanedione as a solid to 260 mL of dry MeCN (KF<100 ug/mL). To the resulting suspension was added 18.5 g (0.13 mol) of Na$_2$HPO$_4$ and the sides of the reaction flask were washed with an additional 100 ml of dry MeCN. In a separate flask containing 150 mL of MeCN was added 56 g (0.195 mol) of POBr$_3$. The resulting POBr$_3$ solution was then added drop-wise to the slurry, and the mixture was heated to 65° C. for 1.5 h and cooled to rt. The reaction mixture was quenched with 1N KOH to a final pH of <8.0 and aged for 30 min. During the quench the precipitation of insolubles occurs at pH<4 which turns to an oily mass around pH 7-7.5. The bottom oily layer and aqueous layer were separated. The top MeCN layer containing the product was filtered over a small plug of solka floc, which was then rinsed with one bed volume of MeCN. The combined MeCN layers were then concentrated to a final volume of 500 mL. To the concentrated solution was added 600 mL of water at rt and the mixture seeded with 500 mg of 3-bromo-2-(4-fluorophenyl)-2-cyclopenten-1-one. After aging for 30 min, the remaining 700 mL of water were added drop-wise. After 45 min, the slurry was filtered, washed with 100 mL of water and dried under vacuum at 25° C. giving 3-bromo-2-(4-fluorophenyl)-2-cyclopenten-1-one as a light brown solid.

To 50 mL of dry dimethylacetamide (DMAC, KF<100 ug/mL) was added 25 g (98 mmol) of 3-bromo-2-(4-fluorophenyl)-2-cyclopenten-1-one as a solid. In a separate 100 mL round-bottom flask was mixed 2.08 g of 5% Pd/C and 40 mL of DMAC. The slurry containing the catalyst was then added to the flask containing the starting bromide and the 100 mL round bottom flask rinsed with an additional 10 mL DMAC. To the reaction mixture was then added 46.7 mL (196 mmol) of N-tributylamine and 20 mL (473 mmol) of MeOH. The resulting reaction flask was purged with nitrogen (5×) and then with CO (5×). The CO pressure was set at 10 psi and the reaction mixture heated at 60° C. for 12 h. The reaction mixture was filtered over a small plug of solka floc to remove the catalyst and the pad washed with MeOH (172 mL). The methanol was removed under reduced pressure. To the mixture was slowly added 8.6 mL of 1N HCl at such a rate to keep the temperature <24° C., and then the batch was seeded with 1 wt % of methyl 2-(4-fluorophenyl)-3-oxo-1-cyclopent-1-enecarboxylate. After aging for 15 min, 163 mL of 1N HCl was added drop-wise over the next 2.5 hours maintaining the temperature <25° C. The slurry was aged at 15-20° C. for 30 min and sampled for supernatant concentration and filtered. The cake is washed with 17 mL of 1 N HCl and then water until the pH of the filtrate was >5. The product is dried under vacuum/nitrogen sweep for 40 h at 25° C. to give methyl 2-(4-fluorophenyl)-3-oxo-1-cyclopent-1-enecarboxylate as a brown solid.

To 13.2 L of toluene was added 900 mL (0.897 mol) of (R)-2-methyl-oxazaborolidine and 540 mL (5.40 mol) of BH$_3$.SMe$_2$ and the mixture was cooled to –20° C. In a separate round bottom flask was added 2.168 Kg (9.26 mol) of methyl 2-(4-fluorophenyl)-3-oxo-1-cyclopent-1-enecarboxylate and 21 L toluene (final KF~100). The toluene solution of ester was then added drop-wise over 1.25 h at such a rate that the internal temperature did not rise above –20° C. After 1.25 h the reaction mixture was quenched by slow addition of 2.2 liter of MeOH and allowed to warm to rt. The resulting toluene solution was washed with 21 L of 1N HCl, and azeotropically dried (50° C., 25 inHg) to a final volume of 21 liters solution of methyl (3S)-2-(4-fluorophenyl)-3-hydroxycyclopent-1-enecarboxylate.

To a toluene stream containing methyl (3S)-2-(4-fluorophenyl)-3-hydroxycyclopent-1-enecarboxylate in 21 L toluene was added 12 Liters of dry THF and the reaction mixture was cooled to –48° C. To the cooled solution was added drop-wise over 45 min 3.8 Liters (13.46 mol) of 70% Red-Al in toluene. The reaction mixture was allowed to warm to –25° C. over 2.5 h and was added to a solution of 21 L of 2M NaHSO$_4$. The mixture was stirred for 30 min and the layers separated. The toluene layer was then washed with 15 L of water. The toluene layer was then azeotropically dried (50° C., 25 inHg) to a final volume of 21 L (KF 130 ug/mL) and used in the next step. To the toluene solution was added 820 mL (3.6 mol) of 25 wt % NaOMe in MeOH at 50° C. and the mixture heated to 75° C. for 1 h. The mixture was then cooled to 50° C. and 17 L of water, 1 L of MeOH, and 4.5 L of 6N NaOH was added. The mixture was stirred at 20-25° C. overnight. The layers were separated, and the toluene layer discarded. The aqueous layer was then washed with 15 L of MTBE and the MTBE layer discarded. The aqueous layer was then made acidic with conc. HCl (2.1 L, pH 1). The mixture was extracted with 40 L of IPAC. The IPAC layer containing the product (1.35 kg, 69% assay) was then treated with 500 g of Darco for 30 min at 25° C. and filtered over a pad of solka floc, rinsing the pad with and additional 5 L of IPAC. The IPAC solution was then azeotropically dried (45° C., 25 inHg) to a final volume of 15 L (KF<200) and cooled to 20° C. To the IPAC solution was added 3.04 L of n-heptane and the mixture seeded with 5 g of (1R,2R,3S)-2-(4-fluorophenyl)-3-hydroxycyclopentane-1-carboxylic acid. After a good seed bed had been formed (30 min) the rest of the n-heptane (40.4 L) was added drop-wise over 1 hour. The slurry was cooled to 10° C. and filtered. The cake was washed with 2 L of 5:1 n-heptane/IPAC and then with 1 L of heptane. The cake was then dried under vacuum/N$_2$ sweep at 20-25° C. overnight to provide (1R,2R,3S)-2-(4-fluorophenyl)-3-hydroxycyclopentane-1-carboxylic acid as a colorless solid.

A solution of (1R,2R,3S)-2-(4-fluorophenyl)-3-hydroxycyclopentane-1-carboxylic acid (9.8 kg) in methanol (49 L) was heated to reflux in the presence of 10 mol % sulfuric acid. The reaction was complete within 3 h (<2% starting material) and after cooling to 20° C., the resulting solution was diluted with dichloromethane (49 L). This solution was then washed with 0.1M Na$_{21}$PO$_4$ (98 L) followed by saturated NaCl$_{(aq)}$ (49 L). The resulting dichloromethane solution of (1R,2R,3S)-2-(4-fluorophenyl)-3-hydroxycyclopentane-1-carboxylic acid methyl ester was then azeotropically dried with DCM (a further 75 L DCM used) to a final volume of 32 L.

(1R)-1-(3,5-bis(Trifluoromethyl)phenyl)ethanol (15 kg) was dissolved in heptane-dichloromethane (4:1; 150 L) and the resulting solution was then treated with DBU (10 mol %) and trichloroacetonitrile (1.05 equiv.) at 20° C. The addition of Cl$_3$CCN resulted in a slight exotherm and the temperature of the batch increased gradually to 27° C. After aging at approx. 25° C. for 6 h, the reaction was complete (4% (S)-BTBA). The resulting reaction mixture was washed with 0.1M citric acid (75 L) followed by saturated NaCl$_{(aq)}$ (75 L). A total of <0.5% product was lost to these washes. The resulting organic layer was then concentrated to a final volume of approx. 67 L ((1R)-1-(3,5-bis(trifluoro-methyl)phenyl)ethoxy)-trichloroacetimidate in dichloromethane.

The solutions of (1R,2R,3S)-2-(4-fluorophenyl)-3-hydroxycyclopentane-1-carboxylic acid methyl ester in dichloromethane and ((1R)-1-(3,5-bis(trifluoromethyl)phenyl)ethoxy)-trichloro-acetimidate (1.25 equiv.) in heptane, prepared above, were combined and cooled to −8° C. Tetrafluoroboric acid (10 mol %) was added and the batch was left to age at this temperature. Additional HBF$_4$ catalyst (2 mol %) was added and the reaction mixture was left to age at −8° C. overnight. After a total of 23 h, the reaction was determined to be complete by HPLC and was warmed to rt. The resulting slurry was solvent-switched to IPA (final volume of 50 L), 5M NaOH$_{(aq)}$ (3 equiv.) was added and the solution was warmed to 40° C. After 1.5 h, the hydrolysis was complete and the batch was cooled to rt. The resulting solution was diluted with water (100 L) and washed twice with heptane (2×100 L). The aqueous layer was then acidified by addition of conc. hydrochloric acid (3.7 equiv.) and extracted twice with heptane (2×100 L). The combined heptane extracts were then washed twice with water (2×100 L) and concentrated to a volume of 100 L. Negligible product was lost to the heptane washes, the acidified aqueous layer and the combined aqueous washes. To the concentrated heptane solution was added MTBE (10 L) and triethylamine at 45° C. The resulting solution was then allowed to cool to 20° C. overnight during which time the ether-acid TEA salt crystallized from solution. The slurry was therefore cooled to 5° C. before filtering. The filtration liquors contained 1.3% of the desired product ((1R),(2R),(3S))-3-((1R)-1-(3,5-bis(trifluoromethyl)phenyl)ethoxy)-2-(4-fluorophenyl)cyclopentane-carboxylic acid ½ TEA salt. The crude TEA salt (12.96 kg) was dissolved in toluene (100 L) and then washed with 1M HCl (55 L) to remove the triethylamine. The resulting organic layer was then washed with saturated aqueous NaHCO$_3$ (50 L) followed by water (50 L). The resulting toluene solution was concentrated to 20 L and heptane (90 L) was added. The resulting solution was warmed to 50° C., triethylamine (1.1 equiv.) was added and the batch was cooled to 30° C. over 1 h. The slurry that had formed was then allowed to cool to 20° C. overnight. The solid was collected by filtration, washing with 9:1 heptane-toluene (2×20 L) to give ((1R),(2R),(3S))-3-((1R)-1-(3,5-bis(trifluoromethyl)phenyl)-ethoxy)-2-(4-fluorophenyl)cyclopentane-carboxylic acid ½ TEA salt. The ½ TEA salt was suspended in water, the water was acidified with 2N HCl until the pH was less than 2, and the mixture was extracted twice with ethyl acetate. The ethyl acetate layers were each successively washed with brine, combined, and dried over sodium sulfate. Removal of solvent in vacuo afforded the free acid as a thick oil which solidified on standing.

EXAMPLE 1

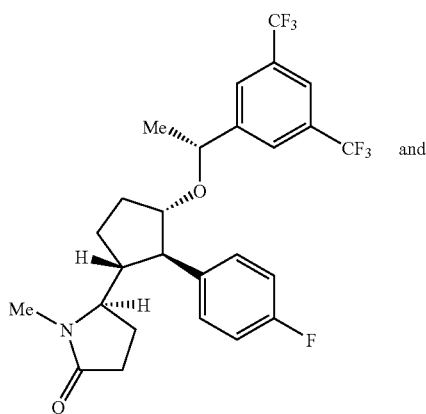

and

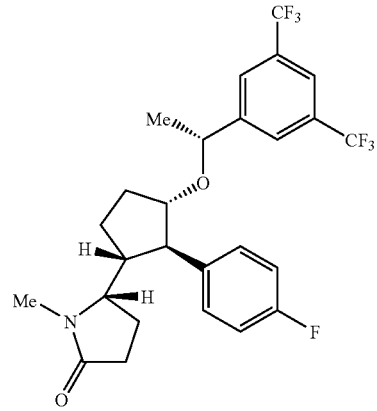

(5R and 5S)-5-(((1R),(2R),(3S))-3-((1R)-1-(3,5-bis(Trifluoromethyl)phenyl)ethoxy)-2-(4-fluorophenyl)cyclopent-1-yl)-1-methylpyrrolidin-2-one Step A: Methyl ((1R),(2R),(3S))-3-((1R)-1-(3,5-bis(trifluoromethyl)phenyl)ethoxy)-2-(4-fluorophenyl)cyclopentanecarboxylate Method A: To a solution of ((1R),(2R),(3S))-3-((1R)-1-(3,5-bis(trifluoromethyl)phenyl)ethoxy)-2-(4-fluorophenyl)cyclopentanecarboxylic acid from Intermediate 1 in 1:1 methylene chloride:methanol was added 2M TMS diazomethane in ether until the yellow color persisted. After 5 min, the excess TMS diazomethane was quenched with acetic acid and the volatiles were removed in vacuo to afford the crude title methyl ester. If necessary, purification by FC [flash chromatography] (20-40% ethyl acetate/hexanes) afforded clean title intermediate. HPLC/MS: m/e=479 (M+1), Rt=4.42 min NMR (CDCl$_3$): δ 1.34 (d, 3 H), 1.86-1.92 (m, 1 H), 2.05-2.1 (m, 3 H), 2.80 (q, 1 H), 3.34 (dd, 1 H), 3.78 (q, 1 H), 4.46 (q, 1 H), 6.85-6.95 (m, 2 H), 6.95-7.05 (m, 2 H), 7.44 (s, 2 H), 7.64 (s, 1 H).

Method B: Into a solution of ((1R),(2R),(3S))-3-((1R)-1-(3,5-bis(trifluoromethyl)phenyl)ethoxy)-2-(4-fluorophenyl)cyclopentanecarboxylic acid from Intermediate 1 in methanol was bubbled HCl gas until the solution was saturated. The solution was aged for 16 hr at rt and was then concentrated in vacuo. The residue was diluted with water and extracted twice with ethyl acetate. The ethyl acetate layers were each successively washed with brine containing sodium bicarbonate solution, combined, and dried over sodium sulfate. Removal of solvent in vacuo and purification by FC (20-40% ethyl acetate/hexanes) afforded the title intermediate.

Step B: ((1R),(2R),(3S))-3-((1R)-1-(3,5-bis(Trifluoromethyl)phenyl)ethoxy)-2-(4-fluorophenyl)cyclopentanemethanol Method A: To a solution of methyl ((1R),(2R),(3S))-3-((1R)-1-(3,5-bis(trifluoromethyl)phenyl)-ethoxy)-2-(4-fluorophenyl)cyclopentanecarboxylate (7.6 gm, 15.9 mmol) from Intermediate 1 in THF (150 mL) cooled in an ice bath was added 2M lithium borohydride in THF (16 mL). After 30 min, the reaction was stirred at rt for 16 hr. The reaction was heated to 40° C. for 5 hr, then quenched with 2N HCl solution, diluted with water, and extracted twice with ethyl acetate. The ethyl acetate layers were each successively washed with brine containing sodium bicarbonate solution, combined, and dried over sodium sulfate. Removal of solvent in vacuo and purification by FC (20-40% ethyl acetate/hexanes) afforded the title intermediate alcohol as a clear oil which gradually solidified. Mass spec (NH$_3$/CI): 451(M+1). NMR (CDCl$_3$): δ 1.34 (d, J=6.5 Hz, 3 H), 1.7-1.85 (m, 2 H), 1.85-2.0 (m, 1 H), 2.0-2.15 (m, 2 H), 2.72 (dd, J=8 and 11 Hz, 1), 3.52 (dABq, J=6.6 and 10.6 Hz, 2 H), 3.68 (q, J=6 Hz, 1 H), 4.47 (q, J=6.5 Hz, 1 H), 6.85-6.95 (m, 2 H), 6.95-7.05 (m, 2 H), 7.40 (s, 2 H), 7.65 (s, 1 H).

Method B: To a suspension of ((1R),(2R),(3S))-3-((1R)-1-(3, 5-bis(trifluoromethyl)phenyl)ethoxy)-2-(4-fluorophenyl)cyclopentanecarboxylic acid ½ TEA salt (25 gm, 48.5 mmol) (see Step A) suspended in toluene (60 mL) and cooled in an ice bath was slowly added 1M borane:THF complex in THF (97 mL). After the initial gas evolution had ceased, the reaction was heated to 75° C. for 1 hr. The reaction was again cooled in an ice bath prior to slow addition of water to quench excess borane. The mixture was diluted with water and extracted twice with ethyl acetate. The ethyl acetate layers were each successively washed with brine containing some sodium bicarbonate solution, combined, dried over sodium sulfate, and concentrated in vacuo. The residue was purified by FC (10-40% ethyl acetate/hexanes) to afford the title intermediate alcohol as a clear oil which gradually solidified. Mass spec (NH$_3$/CI): 451(M+1).

Step C: ((1R),(2R),(3S))-3-((1R)-1-(3,5-bis(Trifluoromethyl)phenyl)ethoxy)-2-(4-fluorophenyl)cyclopentanecarboxaldehyde A solution of oxalyl chloride (1.5 mL) in methylene chloride (40 mL) was cooled in a dry ice/acetone bath and DMSO (2.4 mL) was slowly added. After 15 min, ((1R),(2R),(3S))-3-((1R)-1-(3,5-bis(trifluoromethyl)phenyl)ethoxy)-2-(4-fluorophenyl)cyclopentanemethanol (3.0 gm, 6.7 mmol) from Step B in methylene chloride (10 mL) was added and the reaction was maintained at −70° C. for 1 hr. DIPEA (12 mL) was then added and the reaction was warmed to rt for 2 hr. The reaction was then diluted with water and extracted twice with methylene chloride. The methylene chloride layers were each successively washed with brine containing some sodium bicarbonate solution, combined, dried over sodium sulfate, and concentrated in vacuo. The residue was purified by FC (5% ethyl acetate/hexanes) to afford the title intermediate aldehyde as a clear oil which gradually solidified in the freezer.

Step D: ((1S),(2R),(3R))-1-((1R)-1-(3,5-bis(Trifluoromethyl)phenyl)ethoxy)-2-(4-fluorophenyl)-3-((1R and 1S)-1-hydroxybut-3-en-1-yl)cyclopentane To a solution of ((1R),(2R),(3S))-3-((1R)-1-(3,5-bis(trifluoromethyl)phenyl)ethoxy)-2-(4-fluorophenyl)cyclopentanecarboxaldehyde (1.55 gm, 3.46 mmol) from Step C in THF (20 mL) cooled in an ice bath was added 2M allyl magnesium bromide in THF (2.1 mL). After 30 min TLC still indicated some starting material was left, thus additional 2M allyl magnesium bromide in THF (1 mL) was added. After an additional 90 min at rt, the reaction was quenched into a mixture of water, 2N HCl solution, and ether and the mixture was extracted twice with ether. The ether layers were each successively washed with brine containing some sodium bicarbonate solution, combined, and dried over sodium sulfate. Removal of solvent in vacuo and purification by FC (10-20% ethyl acetate/hexanes) afforded the title intermediate as a mixture of alcohol isomers. HPLC/MS: m/e=-(no ionization), Rt=4.45 min NMR (CDCl$_3$): δ 1.37 (2 d, J=6.5 Hz, 3 H), 1.7-2.25 (4 m, 7 H), 3.00 (m, 1 H), 3.49 (m, 0.5 H), 3.6-3.72 (m 1.5 H), 4.5 (m, 1 H), 4.86-5.1 (m, 2 H), 5.6-5.9 (m, 1 H), 6.93 (2 t, J=8.6 Hz, 2 H), 7.02-7.1 (m, 2 H), 7.45 (s, 2 H), 7.69 (s, 1 H).

Step E: ((1S),(2R),(3R))-1-((1R)-1-(3,5-bis(Trifluoromethyl)phenyl)ethoxy)-2-(4-fluorophenyl)-3-((1R and 1S)-1,4-dihydroxybut-1-yl)cyclopentane To a solution of ((1S),(2R),(3R))-1-((1R)-1-(3,5-bis(trifluoromethyl)phenyl)ethoxy)-2-(4-fluorophenyl)-3-((1R and 1S)-1-hydroxybut-3-en-1-yl)cyclopentane (837 mg, 1.71 mmol) from Step D in THF (8 mL) was added 1M borane: THF complex (2.6 mL). After 1 hr at rt, additional 1M borane: THF complex (1 mL) was added. After an additional 1 hr, 5N sodium hydroxide (0.62 mL) and 30% hydrogen peroxide (1.0 mL) were added. The reaction was stirred at rt for 90 min, then quenched into a mixture of water and ether, and extracted twice with ether. The ether layers were each successively washed with brine containing some sodium bicarbonate solution, combined, and dried over sodium sulfate. Removal of solvent in vacuo and purification by Prep TLC (30-50% ethyl acetate/hexanes) afforded the title intermediate as a mixture of hydroxy isomers. HPLC/MS: m/e=509 (M+1), Rt=3.76 min Step F: Methyl 4-(((1R),(2R),(3S))-3-((1R)-1-(3,5-bis(trifluoromethyl)phenyl)ethoxy)-2-(4-fluorophenyl)cyclopent-1-yl)-4-oxobutanoate To a solution of ((1S),(2R),(3R))-1-((1R)-1-(3,5-bis(trifluoromethyl)phenyl)ethoxy)-2-(4-fluorophenyl)-3-((1R and 1S)-1,4-dihydroxybut-1-yl)cyclopentane (710 mg, 1.4 mmol) from Step E in acetone (10 mL) was added 8N Jones reagent (1.6 mL). The reaction was stirred at rt for 30 min and was then concentrated. The residue was diluted with water and extracted twice with ethyl acetate. The ethyl acetate layers were each successively washed with brine, combined, and dried over sodium sulfate. Removal of solvent in vacuo afforded the crude keto-acid which was used directly for the methylation.

To a solution of the above crude acid in 1:1 methylene chloride:methanol (10 mL) was added 2M TMS diazomethane in ether until the yellow color persisted. After 5 min, the excess TMS diazomethane was quenched with acetic acid and the volatiles were removed in vacuo. The residue was purified by prep TLC (20% ethyl acetate/hexanes) to afford the title compound. HPLC/MS: m/e=535 (M+1), Rt=4.37 min NMR (CDCl$_3$): δ 1.37 (d, J=6.4 Hz, 3 H), 1.84 (m, 1 H), 2.02 (m, 1 H), 2.15 (m, 2 H), 2.34-2.7 (m, 4 H), 2.97 (br q, 1 H), 3.31 (dd, J=8.3 and 10.2 Hz, 1 H), 3.64 (s, 3 H), 3.74 (br q, 1 H), 4.5 (q, J=6.4 Hz, 1 H), 6.93 (t, J=8.6 Hz, 2 H), 7.07 (m, 2 H), 7.43 (s, 2 H), 7.69 (s, 1 H).

Step G: (5R and 5S)-5-(((1R),(2R),(3S))-3-((11R)-1-(3,5-bis(Trifluoromethyl)phenyl)ethoxy)-2-(4-fluorophenyl)cyclopent-1-yl)-1-methylpyrrolidin-2-one To a solution of methyl 4-(((1R),(2R),(3S))-3-((1R)-1-(3, 5-bis(trifluoromethyl)phenyl)-ethoxy)-2-(4-fluorophenyl) cyclopent-1-yl)-4-oxobutanoate (690 mg, 1.29 nmol) prepared as in Step F in 2M methylamine in methanol (5 mL) was added methylamine hydrochloride (172 mg) and 10% Pd/C (100 mg). The mixture was then hydrogenated on a Parr shaker at 50 p.s.i. for 72 hr. The reaction was filtered, solvent evaporated, fresh 2M methylamine in methanol and Pd/C added, and the hydrogenation continued for another 24 hr. Filtration and evaporation gave a residue which was purified by Prep TLC to afford the title compound as a mixture of lactam isomers. HPLC/MS: m/e=518 (M+1), Rt=4.05 min NMR (CDCl$_3$): δ 1.38 (d, J=6.7 Hz, 3 H), 1.6-2.5 (4m, 9 H), 2.36 and 2.67 (2 s, 3 H), 2.75 and 2.79 (2 dd, J 3.2 and 10 Hz, 1 H), 3.60 (dt, J=4.3 and 8.8 Hz, 1 H), 3.67 and 3.75 (2 q, J=6.6 Hz, 1 H), 4.49 (q, J=6.4 Hz, 1 H), 6.9-7.05 (m, 4 H), 7.43 (s, 2 H), 7.69 (s, 1 H).

EXAMPLE 2

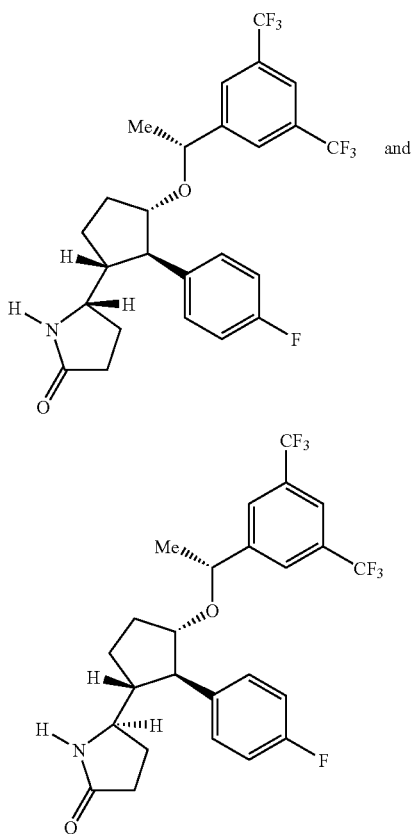

(5R and 5S)-5-(((1R),(2R),(3S))-3-((1R)-1-(3,5-bis(Trifluoromethyl)phenyl)ethoxy)-2-(4-fluorophenyl)cyclopent-1-yl)pyrrolidin-2-one Using essentially the same procedures as in Example 1, Step G, methyl 4-(((1R),(2R),(3S))-3-((R)-1-(3,5-bis(trifluoromethyl)phenyl)ethoxy)-2-(4-fluorophenyl)cyclopent-1-yl)-4-oxobutanoate (100 mg, 0.187 mmol) from Example 1, Step F in 2M ammonia in methanol (5 mL) and ammonium acetate (14 mg) was hydrogenated on a Parr shaker at 50 p.s.i. for 4 days. The reaction was filtered, solvent evaporated, fresh 2M ammonia in methanol and Pd/C added, and the hydrogenation continued for another 3 days. Filtration and evaporation gave a residue which was purified by Prep TLC to afford recovered starting material (15 mg) and title product as a mixture of (5S) and (5R) lactam isomers. HPLC/MS: m/e=504 (M+1), Rt=3.84 min

EXAMPLE 3

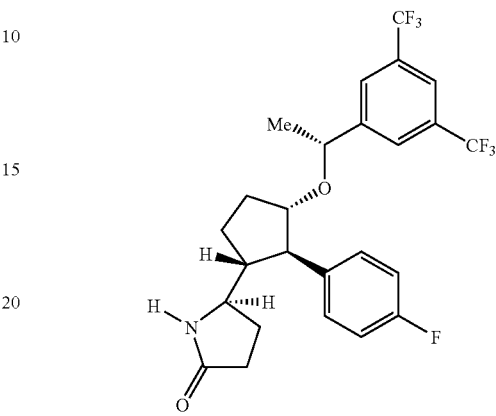

(5R)-5-(((1R),(2R),(3S))-3-((1R)-1-(3,5-bis(Trifluoromethyl)phenyl)ethoxy)-2-(4-fluorophenyl)cyclopent-1-yl)pyrrolidin-2-one Step A: N-Methyl,N-methoxy ((1R),(2R),(3S))-3-((1R)-1-(3,5-bis(trifluoromethyl)phenyl)-ethoxy)-2-(4-fluorophenyl)cyclopentanecarboxamide To a solution of ((1R),(2R),(3S))-3-((1R)-1-(3,5-bis(trifluoromethyl)phenyl)ethoxy)-2-(4-fluorophenyl)cyclopentanecarboxylic acid (10 gm, ~21.4 mmol) from Intermediate 1 (obtained from 11 gm of ½ TEA salt,~21.4 mmol) in methylene chloride (50 mL) was added at rt DMF (3 drops, cat.) followed by slow addition of oxalyl chloride (2.4 mL, 27 mmol). After stirring at rt for 1 hr, the gas evolution had stopped and the reaction was concentrated to dryness in vacuo. The residue was taken up in methylene chloride and reconcentrated twice to remove excess oxalyl chloride.

The above residue was taken up in methylene chloride (100 mL) and cooled in an ice bath before addition of N,O-dimethylhydroxylamine hydrochloride (2.65 gm, 33 mmol) and then DIPEA (11.6 mL, 65 mmol) over 5 min. The reaction was warmed to rt over 30 min and aged for 2 hr. The reaction was then quenched into a mixture of water and 2N HCl (pH<3) and was extracted twice with methylene chloride. The methylene chloride layers were each successively washed with brine containing some sodium bicarbonate solution, combined, and dried over sodium sulfate. Removal of solvent in vacuo afforded the crude product which was purified by FC (10-40% ethyl acetate/hexanes) to afford the title intermediate (10.8 gm) as a thick oil (R$_f$=0.2 in 20% ethyl acetate/hexanes). HPLC/MS: m/e=508 (M+1), Rt=4.15 min NMR (CDCl$_3$): δ 1.41 (d, J=6.7 Hz, 3 H), 1.9-2.0 (m, 1 H), 2.06 (br q, 2 H), 2.16-2.24 (m, 1 H), 3.12 (s, 3 H), 3.22 (m, 1 H), 3.37 (s, 3 H), 3.53 (dd, J=8.9 and 11 Hz, 1 H), 3.84 (q, J=8.5 Hz, 1 H), 4.55 (q, J=6.7 Hz, 1 H), 6.94 (br t, J=8.7 Hz, 2 H), 7.11 (m, 2 H), 7.49 (s, 2 H), 7.73 (s, 1 H).

Step B: ((1S),(2R),(3R))-1-((1R)—-(3,5-bis(Trifluoromethyl)phenyl)ethoxy)-2-(4-fluorophenyl)-3-(1-oxopent-4-en-1-yl)cyclopentane To a solution of N-methyl,N-methoxy ((1R),(2R),(3S))-3-((1R)-1-(3,5-bis(trifluoro-methyl)phenyl)ethoxy)-2-(4-fluorophenyl)cyclopentanecarboxamide (5.0 gm, 9.9 mmol) from Step A in THF (50 mL) cooled in an ice bath was added 0.5M but-3-en-1-yl magnesium bromide in THF (25 mL, 12.5 mmol). The reaction was stirred for 30 min and was then allowed to warm to rt. Since TLC (20% ethyl acetate/hexanes) of an aliquot indicated starting material was still present, another 25 mL portion of 0.5M but-3-en-1-yl magnesium bromide in THF was added. After an additional 2 hr, the reaction was quenched into water containing excess 2N HCl and the mixture was extracted twice with ethyl acetate. The ethyl acetate layers were each successively washed with brine containing some sodium bicarbonate solution, combined, and dried over sodium sulfate. Removal of solvent in vacuo afforded the title intermediate (4.8 gm) as a thick oil which can be used directly in the following step ($R_f$=0.75 in 20% ethyl acetate/hexanes) or preferably be purified by FC (10-20% ethyl acetate/hexanes). HPLC/MS: m/e=503 (M+1), $R_t$=4.53 min NMR (CDCl$_3$): δ 1.40 (d, J=6.6 Hz, 3 H), 1.83-1.92 (m, 1 H), 1.96-2.3 (4 m, 6 H), 2.36-2.44 (m, 1 H), 2.92-3.02 (m, 1 H), 3.33 (dd, J=8.9 and 11 Hz, 1 H), 3.77 (q, J=8.5 Hz, 1 H), 4.52 (q, J=6.6 Hz, 1 H), 4.92 (m, 1 H), 4.95 (m, 1 H), 5.71 (m, 1 H), 6.96 (br t, J=8.7 Hz, 2 H), 7.08 (m, 2 H), 7.46 (s, 2 H), 7.72 (s, 1 H).

Step C: ((1S),(2R),(3R))-1-((1R)-1-(3,5-bis(Trifluoromethyl)phenyl)ethoxy)-2-(4-fluorophenyl)-3-((1S and 1R)-1-(benzyloxycarbonylamino)pent-4-en-1-yl)cyclopentane (higher (1S) and lower (1R) isomers)

Method A: To a solution of 7N ammonia in methanol (20 mL) was added ((1S),(2R),(3R))-1-((1R)-1-(3,5-bis(trifluoromethyl)phenyl)ethoxy)-2-(4-fluorophenyl)-3-(1-oxopent-4-en-1-yl)cyclopentane (2.0 gm, 4.0 mmol) from Step B and ammonium chloride (350 mg, 6.0 mmol). The reaction flask was sealed with a septum and stirred at rt for 60 min, at which time sodium cyanoborohydride (500 mg, 8.0 mmol) was added portionwise over another 30 min. The reaction was stirred at rt for 16 hr, then quenched into water and sodium hydroxide solution, and extracted twice with methylene chloride. The methylene chloride layers were each successively washed with brine containing some sodium hydroxide solution, combined, and dried over sodium sulfate. Removal of solvent in vacuo afforded the crude amine product as a dark oil. HPLC/MS: m/e=504 (M+1); Rt=3.46 min.

The above residue was taken up in methylene chloride (50 mL) and was cooled in an ice bath. To the solution was added DIPEA (3.6 mL, 20 mmol) and benzyl chloroformate (1.7 mL, 12 mmol). The reaction was allowed to warm to rt over 4 hr and was then quenched into water containing excess 2N HCl. The mixture was extracted twice with methylene chloride and the methylene chloride layers were each successively washed with brine containing some sodium bicarbonate solution, combined, and dried over sodium sulfate. Removal of solvent in vacuo afforded the crude CBZ products as a dark oil. This was purified by FC (5-40% ethyl acetate/hexanes) to afford in order of elution: recovered starting material (360 mg), unknown by-product, higher Rf CBZ (1S) product (430 mg), mixed fractions (200 mg), lower Rf (1R) CBZ product (600 mg), and then two isomeric hydroxyl by-products from reduction of the ketone.

Method B: Method B was done essentially the same as Method A except that only 1 eq. of 7M ammonia in methanol and 10 eq. of ammonium acetate are used in place of excess ammonia and ammonium chloride. The yield of each CBZ isomer is about 40%. (Higher Rf (1S) isomer) HPLC/MS: in/e=638 (M+1), 594 (M+1-44, 100%), Rt=4.70 min (Lower Rf (1R) isomer) HPLC/MS: m/e=638 (M+1), 594 (M+1-44, 100%), Rt=4.70 min NMR (CDCl$_3$): δ 1.39 (d, J=6.7 Hz, 3 H), 1.44-1.5 (m, 1 H), 1.6-1.7 (m, 2 H), 1.74-1.9 (m, 2 H), 1.96-2.04 (m, 2 H), 2.04-2.18 (m, 2 H), 2.83 (dd, J=7.8 and 10.6 Hz, 1 H), 3.65 (m, 1 H), 3.72 (q, J=7.3 Hz, 1 H), 4.48-4.54 (m, 2 H), 4.91 (m, 1 H), 4.93 (m, 1 H), 5.13 (ABq, 2 H), 5.71 (m, 1 H), 6.95 (br t, J=8.7 Hz, 2 H), 7.07 (m, 2 H), 7.35-7.43 (m, 5 H), 7.44 (s, 2 H), 7.71 (s, 1 H).

Step D: (5R)-5-(((1R),(2R),(3S))-3-((1R)-1-(3,5-bis(Trifluoromethyl)phenyl)ethoxy)-2-(4-fluorophenyl)cyclopentan-1-yl)-1-benzyloxycarbonylpyrrolidin-2-one (from lower CBZ (1R) isomer)

Method A: A solution of ((1S),(2R),(3R))-1-((1R)-1-(3,5-bis(trifluoromethyl)phenyl)ethoxy)-2-(4-fluorophenyl)-3-((1R)-1-(benzyloxycarbonylamino)pent-4-en-1-yl)cyclopentane (lower (1R) isomer from Step C) (600 mg, 0.94 mmol) in methanol (30 mL) was cooled in a dry ice/acetone bath to −70° C. Ozone was bubbled into the solution until the blue color presisted. Excess ozone was remove with a stream of nitrogen and the ozonide mixture was quenched with dimethyl sulfide (5 mL). The mixture was allowed to warm to rt for 2 hr and 2 drops of 2N HCl were added prior to concentration of the reaction in vacuo. The residue was taken up in acetone (25 mL) and evaporated to remove water. The residue was again taken up in acetone (25 mL) and excess Jones reagent (0.50 mL) was added at rt all at once. After stirring for 2 hr, the reaction was quenched into water and the mixture was extracted twice with ethyl acetate. The ethyl acetate layers were each successively washed with brine containing some sodium bicarbonate solution, combined, and dried over sodium sulfate. Removal of solvent in vacuo and purification by FC (20-40% ethyl acetate/hexanes) afforded the title intermediate.

Method B: Method B was done essentially the same as Method A except that on larger scale the crude ozonolysis product in acetone was slowly added to excess Jones Reagent in acetone at less than 30° C. After 1 hr, the excess Jones Reagent was quenched with isopropanol. Work-up and purification was done as in Method A. HPLC/MS: m/e=638 (M+1), 594 (M+1-44, 100%), Rt=4.35 min NMR (CDCl$_3$): δ 1.34 (d, J=6.5 Hz, 3 H), 1.62-1.8 (m, 2 H), 1.8-1.9 (m, 2 H), 2.0-2.1 (m, 2 H), 2.36-2.58 (m, 2 H), 2.68-2.8 (m, 2 H), 3.52 (q, J=6.2 Hz, 1 H), 4.35 (ddd, 1 H), 4.41 (q, J=6.5 Hz, 1 H), 5.06 (ABq, J=12.4 Hz, 2 H), 6.77 (br t, J=8.6 Hz, 2 H), 6.90 (m, 2 H), 7.15-7.35 (m, 5 H), 7.35 (s, 2 H), 7.64 (s, 1 H).

Step E: (5R)-5-(((1R),(2R),(3S))-1-((1R)-1-(3,5-bis(Trifluoromethyl)phenyl)ethoxy)-2-(4-fluorophenyl)cyclopentan-1-yl)pyrrolidin-2-one (lower (R) isomer)

A solution of (5R)-5-(((1R),(2R),(3S))-1-((1R)-1-(3,5-bis(trifluoromethyl)phenyl)-ethoxy)-2-(4-fluorophenyl)cyclopentan-1-yl)-1-benzyloxycarbonylpyrrolidin-2-one (lower (R) isomer from Step D) (400 mg, 0.63 mmol) in methanol (5 mL) was hydrogenated on a Parr shaker at 50 p.s.i. for 1 hr when TLC indicated the reaction was complete. The reaction was filtered and evaporated. The residue was purified on 6×1000 □M prep plates (3% methanol in methylene chloride) to remove any residual higher Rf isomer and afforded pure title compound. HPLC/MS: m/e=504 (M+1), Rt=3.85 min NMR (CDCl₃): δ 1.38 (d, J=6.6 Hz, 3 H), 1.4-1.53 (m, 1 H), 1.68-1.88 (m, 2 H), 1.88-2.0 (m, 2 H), 2.0-2.15 (m, 2 H), 2.2-2.26 (m, 2 H), 2.69 (dd, J=7.2 and 10.1 Hz, 1 H), 3.61 (q, J=6.9 Hz, 1 H), 3.66 (q, J=5.9 Hz, 1 H), 4.49 (q, J=6.6 Hz, 1 H), 6.16 (s, 1 H), 6.95 (br t, J=8.6 Hz, 2 H), 7.01 (m, 2 H), 7.42 (s, 2 H), 7.69 (s, 1 H).

EXAMPLE 4

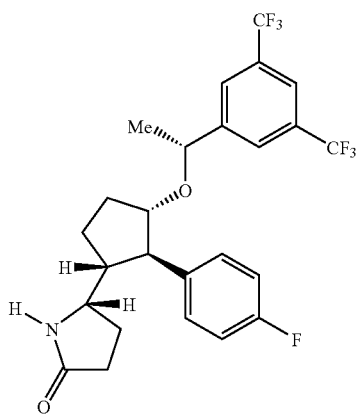

(5S)-5-(((1R),(2R),(3S))-3-((1R)-1-(3,5-bis(Trifluoromethyl)phenyl)ethoxy)-2-(4-fluorophenyl)cyclopentan-1-yl)pyrrolidin-2-one Using essentially the same procedures as in Example 3, Step D-E, ((1S),(2R),(3R))-1-((1R)-1-(3,5-bis(trifluoromethyl)phenyl)ethoxy)-2-(4-fluorophenyl)-3-((1S)-1-(benzyloxycarbonyl-amino)pent-4-en-1-yl)cyclopentane (higher (1S) isomer from Example 3, Step C) (60 mg, 0.094 mmol) was converted to the title compound. HPLC/MS: m/e=504 (M+1), Rt=3.95 min NMR (CDCl₃): δ 1.37 (d, J=6.4 Hz, 3 H), 1.56-1.68 (m, 1 H), 1.68-1.86 (m, 2 H), 1.86-1.98 (m, 2 H), 1.98-2.16 (m, 2 H), 2.2-2.26 (m, 2 H), 2.74 (dd, J=7.8 and 10.5 Hz, 1 H), 3.58 (q, J=7.2 Hz, 1 H), 3.66 (q, J=5.9 Hz, 1 H), 4.47 (q, J=6.6 Hz, 1 H), 5.08 (s, 1 H), 6.97 (br t, J=8.6 Hz, 2 H), 7.05 (m, 2 H), 7.42 (s, 2 H), 7.69 (s, 1 H).

EXAMPLE 6

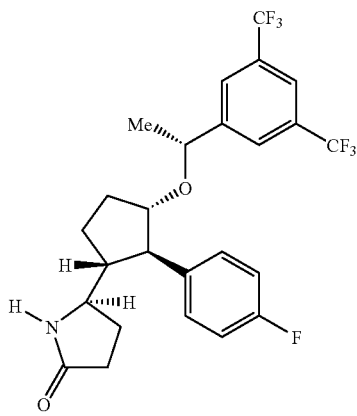

(5R)-5-(((1R),(2R),(3S))-3-((1R)-1-(3,5-bis(Trifluoromethyl)phenyl)ethoxy)-2-(4-fluorophenyl)-cyclopentan-1-yl)-5-methylpyrrolidin-2-one Step A: ((1S),(2R),(3R))-1-((1R)-1-(3,5-bis(Trifluoromethyl)phenyl)ethoxy)-2-(4-fluorophenyl)-3-((2R and 2S)-2-hydroxyhex-5-en-2-yl)cyclopentane To a solution of ((1S),(2R),(3R))-1-((1R)-1-(3,5-bis(trifluoromethyl)phenyl)ethoxy)-2-(4-fluorophenyl)-3-(1-oxopent-4-en-1-yl)cyclopentane (5.0 gm, 10 mmol) prepared as in Example 3, Step B, in THF (50 mL) was added at rt 1.4M methyl magnesium bromide (10.7 mL). After 1 hr, additional Grignard (5 mL) was added and the reaction was stirred for another hr. The reaction was then quenched into water containing excess 2N HCl and the mixture was extracted twice with ethyl acetate. The ethyl acetate layers were each successively washed with brine containing some sodium bicarbonate solution, combined, and dried over sodium sulfate. Removal of solvent in vacuo and purification by FC (10-30% ethyl acetate/hexanes) afforded partial separation of both title isomeric intermediates (5.15 gm). NMR (CDCl₃)(Higher Rf): δ 1.05 (s, 3 H), 1.38 (d, J=6.6 Hz, 3 H), 1.46 (t, J=7.8 Hz, 2 H), 1.72-1.82 (m, 1 H), 1.82-2.06 (m, 5 H), 2.24 (q, J=7.6 Hz, 1 H), 3.12 (dd, J=6.7 and 9.0 Hz, 1 H), 3.55 (q, J=6.3 Hz, 1 H), 4.51 (q, J=6.6 Hz, 1 H), 4.88-4.95 (m, 2 H), 5.73 (tdd, 1 H), 6.93 (br t, J=8.6 Hz, 2 H), 7.04-7.09 (m, 2 H), 7.45 (s, 2 H), 7.69 (s, 1 H). NMR (CDCl₃) (Lower Rf): δ 1.15 (s, 3 H), 1.38 (d, J=6.6 Hz, 3 H), 1.45 (tABq, 2 H), 1.74-1.90 (m, 4 H), 1.96-2.06 (m, 2 H), 2.23 (q, J=7.6 Hz, 1 H), 3.12 (dd, J=6.4 and 9.0 Hz, 1 H), 3.57 (q, J=6.0 Hz, 1 H), 4.51 (q, J=6.6 Hz, 1 H), 4.81-4.87 (3 m, 2 H), 5.59-5.70 (m, 1 H), 6.93 (br t, J=8.6 Hz, 2 H), 7.06-7.11 (m, 2 H), 7.46 (s, 2 H), 7.70 (s, 1 H).

Step B: ((1S),(2R),(3R))-1-((1R)-1-(3,5-bis(Trifluoromethyl)phenyl)ethoxy)-2-(4-fluorophenyl)-3-((2R and 2S)-2-(acetylamino)hex-5-en-2-yl)cyclopentane To a solution of ((1S),(2R),(3R))-1-((1R)-1-(3,5-bis(trifluoromethyl)phenyl)ethoxy)-2-(4-fluorophenyl)-3-((2R and 2S)-2-hydroxyhex-5-en-2-yl)cyclopentane (5.1 gm, 9.8 mmol) from Step A (mix fractions) in acetonitrile (150 mL) at rt was added conc. sulfuric acid (5 mL). After 2 hr, the reaction was quenched into sodium bicarbonate solution and was extracted twice with ethyl acetate. The ethyl acetate layers were each successively washed with brine containing some sodium bicarbonate solution, combined, and dried over sodium sulfate. Removal of solvent in vacuo and purification by FC (10-40% ethyl acetate/hexanes) separated a major non-polar by-product, a trace of starting material, followed by the higher Rf (2S) title intermediate (700 mg) and lower Rf (2R) title intermediate (800 mg) (Rf=0.15 and 0.25 in 30% ethyl acetate/hexanes). HPLC/MS: m/e=560 (M+1), Rt=4.37 min NMR (CDCl₃)(Higher Rf): δ 1.28 (s, 3 H), 1.39 (d, J=6.5 Hz, 3 H), 1.39 (s, 3 H), 1.56-1.66 (m, 1 H), 1.66-1.95 (m, 5 H), 1.97-2.08 (m, 1 H), 2.12-2.21 (m, 1 H), 2.77 (q, J=7.6 Hz, 1 H), 2.97 (dd, J=6.7 and 9.0 Hz, 1 H), 3.59 (q, J=6.3 Hz, 1 H), 4.49 (q, J=6.6 Hz, 1 H), 4.84-4.91 (3 m, 2 H), 5.25 (s, 1 H), 5.71 (tdd, 1 H), 6.95 (br t, J=8.6 Hz, 2 H), 7.04-7.09 (m, 2 H), 7.44 (s, 2 H), 7.70 (s, 1 H). HPLC/MS: m/e=560 (M+1), Rt=4.37 min NMR (CDCl₃)(Lower Rf): δ 1.31 (s, 3 H), 1.40 (d, J=6.6 Hz, 3 H), 1.45 (m, 1 H), 1.67 (s, 3 H), 1.72-1.83 (m, 2 H), 1.83-2.04 (m, 5 H), 2.86-2.97 (m, 2 H), 3.57 (q, J=6.0 Hz, 1 H), 4.51 (q, J=6.6 Hz, 1 H), 4.88-4.95 (3 m, 2 H), 5.24 (br s, 1 H), 5.65-5.76 (m, 1 H), 6.93 (br t, J=8.6 Hz, 2 H), 7.03-7.08 (m, 2 H), 7.47 (s, 2 H), 7.70 (s, 1 H).

Step C: N-Acetyl (5R)-5-(((1R),(2R),(3S))-3-((1R)-1-(3,5-bis(Trifluoromethyl)phenyl)ethoxy)-2-(4-fluorophenyl)cyclopentan-1-yl)-5-methylpyrrolidin-2-one Using essentially the same procedure as in Example 3, Step D, but using the lower Rf ((1S),(2R),(3R))-1-((1R)-1-(3,5-bis(trifluoromethyl)phenyl)ethoxy)-2-(4-fluorophenyl)-3-((2R)-2-(acetylamino)hex-5-en-2-yl)cyclopentane (800 mg, 1.4 mmol) from Step B, the title intermediate was obtained after FC (15-30% ethyl acetate/hexanes). HPLC/MS: m/e=560 (M+1), Rt=4.32 min NMR (CDCl$_3$): δ 1.38 (d, J=6.7 Hz, 3 H), 1.55 (s, 3 H), 1.73 (s, 3 H), 1.65-1.84 (m, 3 H), 1.91-1.99 (m, 1 H), 2.05-2.15 (m, 1 H), 2.35-2.42 (m, 1 H), 2.55-2.61 (m, 2 H), 2.71 (dd, J=7.1 and 11 Hz, 1 H), 3.39 (q, J=10.5 Hz, 1 H), 3.57 (q, J=6.4 Hz, 1 H), 4.51 (q, J=6.6 Hz, 1 H), 6.88-6.96 (m, 4 H), 7.39 (s, 2 H), 7.70 (s, 1 H).

Step D: (5R)-5-(((1R),(2R),(3S))-3-((1R)-1-(3,5-bis(Trifluoromethyl)phenyl)ethoxy)-2-(4-fluorophenyl)cyclopentan-1-yl)-5-methylpyrrolidin-2-one To a solution of N-acetyl (5R)-5-(((1R),(2R),(3S))-3-((1R)-1-(3,5-bis(trifluoromethyl)-phenyl)ethoxy)-2-(4-fluorophenyl)cyclopentan-1-yl)-5-methylpyrrolidin-2-one (330 mg, 0.59 mmol) from Step C in isopropanol (20 mL) was added hydrazine (0.20 mL). After stirring for 24 hr at rt, additional hydrazine (0.10 mL) was added and the mixture was heated to 60° C. for 4 hr. The reaction was then concentrated in vacuo and the residue was diluted with water, acidified with 2N HCl, and extracted twice with ethyl acetate. The ethyl acetate layers were each successively washed with brine containing some sodium bicarbonate solution, combined, and dried over sodium sulfate. Removal of solvent in vacuo and purification by FC (40-75% ethyl acetate/hexanes, then 5% methanol/ethyl acetate) afforded the title product. HPLC/MS: m/e=518 (M+1), Rt=3.97 min NMR (CDCl$_3$): δ 1.22 (s, 3 H), 1.39 (d, J=6.6 Hz, 3 H), 1.58-1.66 (m, 1 H), 1.71-1.96 (m, 4 H), 2.03-2.13 (m, 1 H), 2.21-2.30 (m, 2 H), 2.21-2.41 (m, 1 H), 2.81 (dd, J=6.8 and 9.4 Hz, 1 H), 3.61 (q, J=6.2 Hz, 1 H), 4.50 (q, J=6.4 Hz, 1 H), 6.20 (s, 1 H), 6.94 (br t, J=8.5 Hz, 2 H), 7.03-7.08 (m, 2 H), 7.44 (s, 2 H), 7.70 (s, 1 H).

EXAMPLE 7

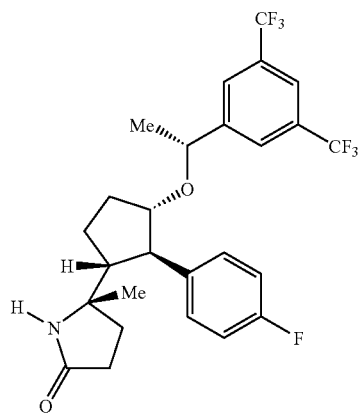

(5S)-5-(((1R),(2R),(3S))-3-((1R)-1-(3,5-bis(Trifluoromethyl)phenyl)ethoxy)-2-(4-fluorophenyl)cyclopentan-1-yl)-5-methylpyrrolidin-2-one Using essentially the same procedure as in Example 6, Steps C-D, but using the higher Rf ((1S),(2R),(3R))-1-((1R)-1-(3,5-bis(trifluoromethyl)phenyl)ethoxy)-2-(4-fluorophenyl)-3-((2S)-2-(acetylamino)hex-5-en-2-yl)cyclopentane (5.8 g) prepared as in Example 6, Step B, the title product was obtained after column chromatography (2% methanol/methylene chloride). HPLC/MS: m/e=518 (M+1), Rt=3.99 min

EXAMPLE 8

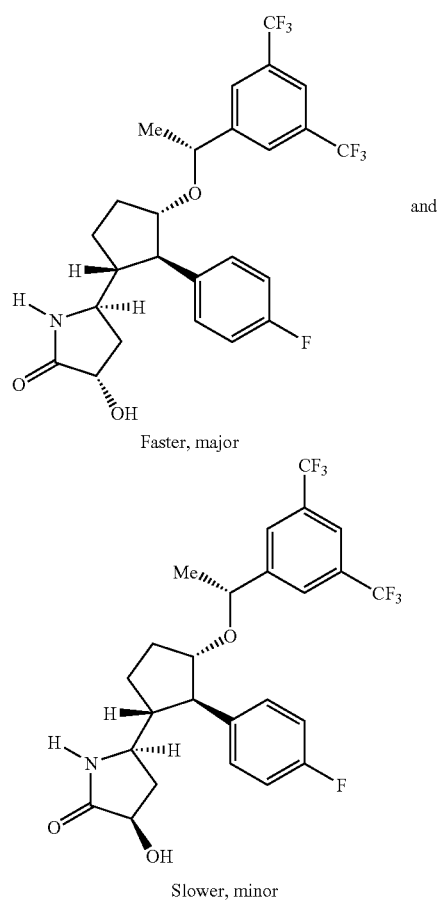

Faster, major

Slower, minor (3R,5R and 3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-hydroxypyrrolidin-2-one Step A: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-1-benzyloxycarbonyl-3-hydroxypyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-1-benzyloxycarbonylpyrrolidin-2-one (0.91 gm, 1.43 mmol) prepared as in Example 3, Step D (from lower (1R) CBZ isomer of Step C) in THF (40 mL) was cooled to −70° C. and 1M LiHMDS (2.1 mL) was added. After 10 min, the mixture was allowed to warm to −20° C. for 30 min after which time solid, dried MoOPH reagent (1.24 gm) was added. The reaction was stirred at rt for 40 min before being quenched with an aq. solution of sodium sulfite and 2N HCl. The mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (30-40% ethyl acetate/hexanes) afforded the title intermediate as a mixture of isomers. HPLC/MS: m/e=610 (M+1-44, 100%), 654 (M+1), Rt=4.18 min Step B: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-3-hydroxypyrrolidin-2-one A solution of (3R,5R and 3S,5R)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonyl-3-hydroxypyrrolidin-2-one (320 mg) from Step A was hydrogenated as in Example 3, Step E, to afford the title product (225 mg) as a mixture of hydroxy isomers. Some of this mixture was then separated using a preparative Chiracel OD column eluting with 15% isopropanol/heptanes to afford the major, faster (3S,5R) isomer and minor, slower (3R,5R) isomer. Faster product; HPLC/MS: m/e=520 (M+1), Rt=3.72 min. NMR (CDCl₃): δ 1.39 (d, J=6.6 Hz, 3 H), 1.63-1.72 (m, 1 H), 1.78-1.87 (m, 1 H), 1.87-1.98 (m, 2 H), 1.98-2.06 (m, 2 H), 2.06-2.15 (m, 1 H), 2.70 (dd, J=7.4 and 10.4 Hz, 1 H), 3.62-3.71 (m, 2 H), 4.23 (t, J=7.3 Hz, 1 H), 4.50 (q, J=6.4 Hz, 1 H), 6.51 (s, 1 H), 6.97 (br t, J=8.5 Hz, 2 H), 7.03-7.08 (m, 2 H), 7.44 (s, 2 H), 7.70 (s, 1 H). Slower product; HPLC/MS: m/e=520 (M+1), Rt=3.73 min. NMR (CDCl₃): δ 1.38 (d, J=6.6 Hz, 3 H), 1.71-1.88 (m, 2 H), 1.88-2.04 (m, 2 H), 2.04-2.15 (m, 2 H), 2.26-2.34 (m, 1 H), 2.81 (dd, J=7.3 and 10 Hz, 1 H), 3.53 (m, 1 H), 3.59 (q, J=8.9 Hz, 1 H), 4.25 (t, J=9.1 Hz, 1 H), 4.52 (q, J=6.4 Hz, 1 H), 6.97 (br t, J=8.5 Hz, 2 H), 7.03-7.08 (m, 2 H), 7.44 (s, 1 H), 7.46 (s, 2 H), 7.72 (s, 1 H).

EXAMPLE 9

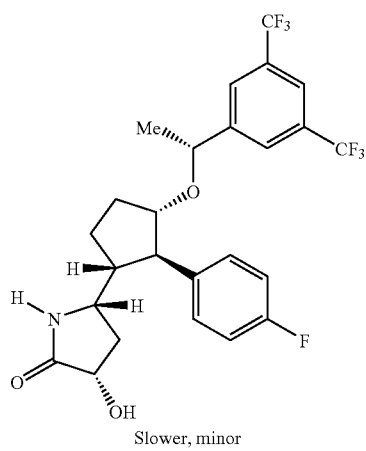

Slower, minor (3R,5S and 3S,5S)-5-(((1R),(2R),(3S))-3-((1R)-1-(3,5-bis(Trifluoromethyl)phenyl)ethoxy)-2-(4-fluorophenyl)cyclopentan-1-yl)-3-(hydroxy)pyrrolidin-2-one Using essentially the same procedures as in Example 8, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonylpyrrolidin-2-one (1.3 gm, 2.0 mmol) prepared as in Example 4 (from higher (1S) CBZ isomer of Example 3, Step C), the title compounds were prepared as a mixture. The isomers can be separated as the CBZ derivative by FC (30-60% ethyl acetate/hexanes) or as the title compounds using a preparative Chiracel OD column (10% isopropanol/heptanes) to afford the major, faster (3R, 5S) isomer (Rt=26 min) and minor, slower (3S,5S) isomer (Rt=32 min). HPLC/MS (Faster): m/e=520 (M+1), Rt=3.73 min HPLC/MS (Slower): m/e=520 (M+1), Rt=3.73 min

EXAMPLE 10

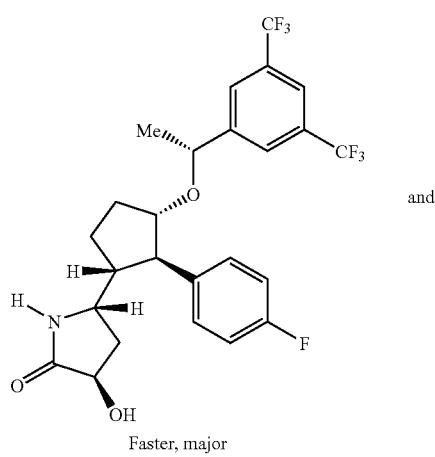

Faster, major and

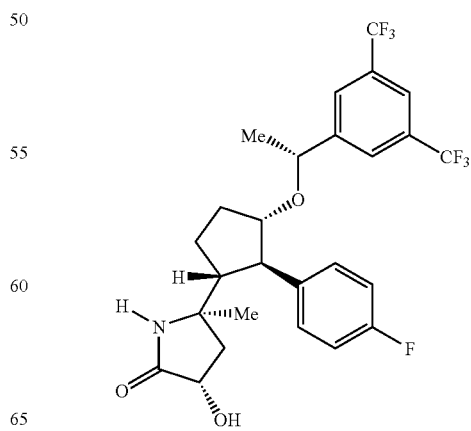

and

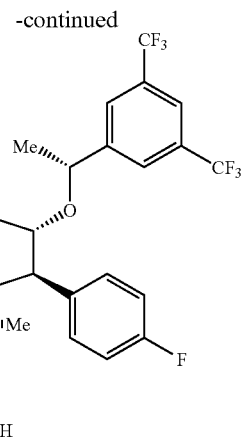

(3R,5R and 3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-hydroxy-5-methylpyrrolidin-2-one Step A: (5R)-5-(((1R),(2R),(3S))-3-((1R)-1-(3,5-bis(Trifluoromethyl)phenyl)ethoxy)-2-(4-fluorophenyl)cyclopentan-1-yl)-1-benzyloxycarbonyl-5-methylpyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-5-methylpyrrolidin-2-one (1.0 gm, 1.9 mmol) prepared as in Example 6, Step D (from lower (1R) acetylamino isomer of Step C) in THF (10 mL) was cooled to −70° C. and 1M LiHMDS (3.8 mL) was added. After 30 min, benzyl chloroformate (0.552 mL) was added and the reaction was allowed to warm to rt for 1 hr. The mixture was quenched into water and aq. 2N HCl and extracted twice with ethyl acetate. The ethyl acetate layers were each successively washed with brine containing some sodium bicarbonate solution, combined, and dried over sodium sulfate. Removal of solvent in vacuo and purification by FC (10-30% ethyl acetate/hexanes) afforded the title intermediate and recovered starting material. HPLC/MS: m/e=608 (M+1-44, 100%), 652 (M+1); Rt=4.48 min Step B: (3R,5R and 3S,5R)-5-(((1R),(2R),(3S))-3-((1R)-1-(3,5-bis(Trifluoromethyl)-phenyl)ethoxy)-2-(4-fluorophenyl)cyclopentan-1-yl)-1-benzyloxycarbonyl-3-hydroxy-5-methylpyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-1-benzyloxycarbonyl-5-methylpyrrolidin-2-one (0.535 gm, 0.85 mmol) prepared in Step A in THF (20 mL) was cooled to −70° C. and 1M LiHMDS in THF (1.0 mL) was added. After 10 min, the mixture was allowed to warm to −20° C. for 30 min after which time solid MoOPH reagent (740 mg) was added. The reaction was stirred at rt for 40 min before being quenched with an aq. solution of sodium sulfite and 2N HCl. The mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (20-40% ethyl acetate/hexanes) afforded recovered starting material and the title intermediate as a mixture of isomers. HPLC/MS: m/e=624 (M+1-44, 100%), 668 (M+1); Rt=4.26 min Step C: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-3-hydroxy-5-methylpyrrolidin-2-on A solution of (3R,5R and 3S,5R)-5-(((1R),(2R),(3S))-3-((1R)-1-(3,5-bis(trifluoromethyl)-phenyl)ethoxy)-2-(4-fluorophenyl)cyclopentan-1-yl)-1-benzyloxycarbonyl-3-hydroxy-5-methylpyrrol-idin-2-one (300 mg) from Step B was hydrogenated as in Example 3, Step E, to afford the title product (226 mg) as a mixture of hydroxy isomers. The isomers were then separated using a preparative Chiracel OD column eluting with 10% isopropanol/heptanes to afford the faster, minor (3R,5R) isomer and slower, major (3S,5R) isomer. HPLC/MS (Faster, minor): m/e=534 (M+1), Rt=4.13 min. NMR (CDCl₃): δ 1.26 (s, 3 H), 1.41 (d, J=6.4 Hz, 3 H), 1.74-1.86 (m, 2 H), 1.86-1.97 (m, 2 H), 2.20-2.11 (m, 1 H), 2.12-2.18 (m, 1 H), 2.30 (q, J=8.7 Hz, 1 H), 2.94 (dd, J=6.4 and 9.2 Hz, 1 H), 3.61 (q, J=5.7 Hz, 1 H), 4.40 (t, J=7.6 Hz, 1 H), 4.52 (q, J=6.4 Hz, 1 H), 5.83 (br s, 1 H), 6.96 (br t, J=8.7 Hz, 2 H), 7.02-7.07 (m, 2 H), 7.47 (s, 2 H), 7.72 (s, 1 H). HPLC/MS (Slower, major): m/e=534 (M+1), Rt=4.08 min. NMR (CDCl₃): δ 1.31 (s, 3 H), 1.41 (d, J=6.6 Hz, 3 H), 1.67 (dd, J=7.1 and 13.7, 1 H), 1.66-1.76 (m, 1 H), 1.76-1.86 (m, 1 H), 1.87-1.96 (m, 1 H), 2.08 (hex, 1 H), 2.23 (q, J=9.8 Hz, 1 H), 2.19 (dd, J=7.1 and 13.7 Hz, 1 H), 2.76 (dd, J=6.8 and 9.9 Hz, 1 H), 3.61 (q, J=6.2 Hz, 1 H), 4.30 (dd, J=7.4 and 8.5 Hz, 1 H), 4.50 (q, J=6.6 Hz, 1 H), 6.16 (br s, 1 H), 6.96 (br t, J=8.7 Hz, 2 H), 7.02-7.07 (m, 2 H), 7.44 (s, 2 H), 7.72 (s, 1 H).

EXAMPLE 11

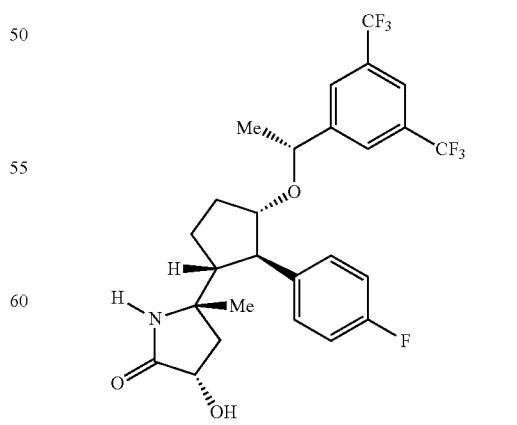

and

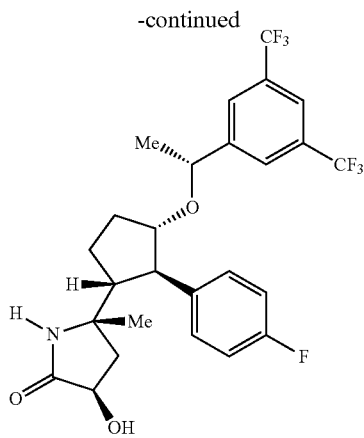

(3R,5S and 3S,5S)-5-(((1R),(2R),(3S))-3-((1R)-1-(3,5-bis(Trifluoromethyl)phenyl)ethoxy)-2-(4-fluorophenyl)cyclopentan-1-yl)-3-hydroxy-5-methylpyrrolidin-2-one Using essentially the same procedures as in Example 10, but starting with (5S)-5-(((1R),(2R),(3S))-3-((1R)-1-(3,5-bis(trifluoromethyl)phenyl)ethoxy)-2-(4-fluorophenyl)cyclopentan 1-yl)-1-benzyloxycarbonyl-5-methylpyrrolidin-2-one (1.0 gm, 1.9 mmol) prepared as in Example 7 (from higher (1S) acetyl isomer of Example 6, Step B), the title compounds were prepared as a mixture. The isomers were separated using a preparative Chiracel OD column (15% isopropanol/heptanes) to afford the major, faster (3S,5S) isomer and minor, slower (3S,5R) isomer. Faster product; HPLC/MS: m/e=534 (M+1), Rt=3.78 min. NMR (CDCl$_3$): δ 1.32 (s, 3 H), 1.40 (d, J=6.7 Hz, 3 H), 1.64-1.74 (m, 1 H), 1.77 (dd, J=7.1 and 13.5, 1 H), 1.74-1.83 (m, 1 H), 1.91-2.00 (m, 1 H), 2.07 (hex, 1 H), 2.23 (q, J=9.8 Hz, 1 H), 2.37 (dd, J=7.1 and 13.5 Hz, 1 H), 2.84 (dd, J=7.4 and 10.3 Hz, 1 H), 3.59 (q, J=6.2 Hz, 1 H), 4.27 (dd, J=7.4 and 8.5 Hz, 1 H), 4.48 (q, J=6.6 Hz, 1 H), 5.62 (br s, 1 H), 6.98 (br t, J=8.7 Hz, 2 H), 7.05-7.10 (m, 2 H), 7.43 (s, 2 H), 7.71 (s, 1 H). Slower product; HPLC/MS: m/e=534 (M+1), Rt=3.80 min.

EXAMPLE 12

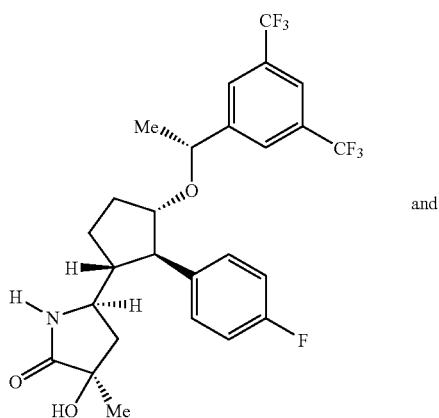

and

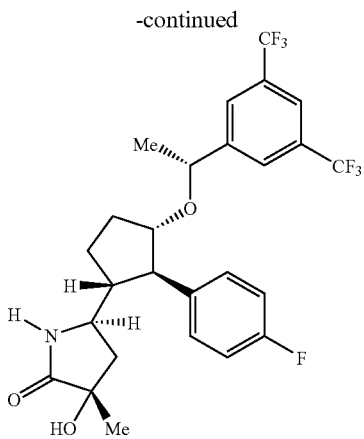

(3R,5R and 3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-hydroxy-3-methylpyrrolidin-2-one Step A: (5R)-5-(((1R),(2R),(3S))-3-((1R)-1-(3,5-bis(Trifluoromethyl)phenyl)ethoxy)-2-(4-fluorophenyl)cyclopentan-1-yl)-3-oxoypyrrolidin-2-one To a solution of (3R,5R and 3S,5R)-5-(((1R),(2R),(3S))-3-((1R)-1-(3,5-bis(trifluoro-methyl)phenyl)ethoxy)-2-(4-fluorophenyl)cyclopentan-1-yl)-3-hydroxypyrrolidin-2-one (0.20 gm, 0.39 mmol) prepared as in Example 8 in acetone (3 mL) was added 8N Jones reagent (0.150 mL). After 30 min, the mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (2% methanol/methylene chloride) afforded the title intermediate. HPLC/MS: m/e=518 (M+1).

Step B: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-3-hydroxy-3-methylpyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-3-oxoypyrrolidin-2-one (62 mg, 0.12 mmol) from Step A in THF (2 mL) was added at rt 1.4 M methyl magnesium bromide (0.146 mL). After 1 hr, the reaction was quenched into with water and 2N HCl and extracted twice with ethyl acetate. The ethyl acetate layers were each successively washed with brine containing some sodium bicarbonate solution, combined, and dried over sodium sulfate. Removal of solvent in vacuo and purification by Prep TLC (2% methanol/methylene chloride) afforded the title products as a mixture of isomers. These were separated on a Chiracel OD column (6% isopropanol/heptanes). Faster isomer; HPLC/MS: m/e=534 (M+1), Rt=3.73 min. NMR (CDCl$_3$): δ 1.32 (s, 3 H), 1.41 (d, J=6.5 Hz, 3 H), 1.6-1.79 (m, 2 H), 1.80-1.91 (m, 1 H), 1.91-2.01 (m, 1 H), 2.01-2.16 (m, 3 H), 2.41 (br s, 1 H), 2.74 (dd, J=7.4 and 10.3 Hz, 1 H), 3.69 (q, J=6.2 Hz, 1 H), 3.74 (q, J=6.9 Hz, 1 H), 4.52 (q, J=6.6 Hz, 1 H), 6.03 (br s, 1 H), 6.98 (br t, J=8.7 Hz, 2 H), 7.02-7.07 (m, 2 H), 7.46 (s, 2 H), 7.72 (s, 1 H). Slower isomer; HPLC/MS:

m/e=534 (M+1), Rt=3.71 min. NMR (CDCl$_3$): δ 1.36 (s, 3 H), 1.42 (d, J=6.6 Hz, 3 H), 1.67 (dd, 1 H), 1.74-1.91 (m, 3 H), 1.94-2.04 (m, 2 H), 2.06-2.18 (m, 2 H), 2.79 (dd, J=7.1 and 9.8 Hz, 1 H), 3.50 (dt, J=8.0 and 8.5 Hz, 1 H), 3.68 (q, J=5.7 Hz, 1 H), 4.53 (q, J=6.4 Hz, 1 H), 6.33 (br s, 1 H), 6.97 (br t, J=8.7 Hz, 2 H), 7.03-7.08 (m, 2 H), 7.47 (s, 2 H), 7.73 (s, 1 H).

EXAMPLE 13

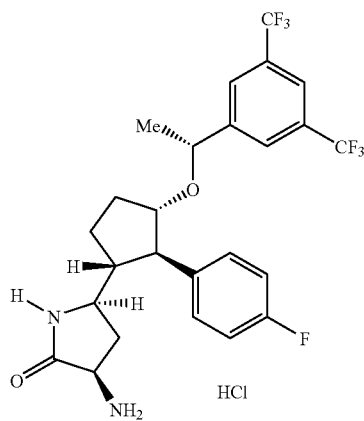

(3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-aminopyrrolidin-2-one hydrochloride salt Step A: (3R,5R and 3S,5R)-5-(((1R),(2R),(3S))-3-((1R)-1-(3,5-bis(Trifluoromethyl)-phenyl)ethoxy)-2-(4-fluorophenyl)cyclopentan-1-yl)-3-mesylpyrrolidin-2-one To a solution of (3R,5R and 3S,5R)-5-(((1R),(2R),(3S))-3-((1R)-1-(3,5-bis(trifluoromethyl)phenyl)ethoxy)-2-(4-fluorophenyl)cyclopentan-1-yl)-3-hydroxypyrrolidin-2-one (0.295 gm, 0.57 mmol) prepared as in Example 8 (prior to separation of the hydroxy isomers) in methylene chloride (3 mL) cooled in an ice bath were added TEA (0.094 mL) and mesyl chloride (0.044 mL). After 10 min, the mixture was allowed to warm to rt for 30 min at which time additional TEA (0.040 mL) and mesyl chloride (0.020 mL) were added. The reaction was stirred at rt for 20 min before being quenched into dilute aq. HCl. The mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (25-50% ethyl acetate/hexanes) afforded the title intermediates as the major, higher Rf (3S,5R) isomer and minor, lower Rf (3R,5R) isomer.

Step B: (3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-azidopyrrolidin-2-one To a solution of (3S,5R)-5-(((1R),(2R),(3S))-3-((1R)-1-(3,5-bis(trifluoromethyl)phenyl)-ethoxy)-2-(4-fluorophenyl)cyclopentan-1-yl)-3-mesylpyrrolidin-2-one (170 mg, 0.284 mmol) from Step A (higher Rf) in DMF (2 mL) was added sodium azide (185 mg). The reaction was heated at 80° C. for 16 hr. The mixture was diluted with water and extracted twice with ether. The ether layers were each successively washed with brine containing some sodium bicarbonate solution, combined, and dried over sodium sulfate. Removal of solvent in vacuo and purification by FC (25-50% ethyl acetate/hexanes) afforded the title intermediate. HPLC/MS: m/e=545 (M+1), Rt=4.13 min. NMR (CDCl$_3$): δ 1.3-1.4 (m, 1 H), 1.42 (d, J=6.4 Hz, 3 H), 1.71-1.81 (m, 1 H), 1.81-1.91 (m, 1 H), 1.94-2.03 (m, 1 H), 2.06-2.16 (m, 2 H), 2.23-2.30 (m, 1 H), 2.75 (dd, J=7.1 and 9.8 Hz, 1 H), 3.57 (q, J=8.0 Hz, 1 H), 3.68 (q, J=6.0 Hz, 1 H), 4.07 (t, J=9 Hz, 1 H), 4.52 (q, J=6.4 Hz, 1 H), 6.49 (br s, 1 H), 6.98 (br t, J=8.7 Hz, 2 H), 7.03-7.08 (m, 2 H), 7.46 (s, 2 H), 7.72 (s, 1 H).

Step C: (3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-aminoopyrrolidin-2-one hydrochloride salt A solution of (3R,5R)-5-(((1R),(2R),(3S))-3-((1R)-1-(3,5-bis(trifluoromethyl)phenyl)ethoxy)-2-(4-fluorophenyl)cyclopentan-1-yl)-3-azidopyrrolidin-2-one (112 mg) from Step B was hydrogenated over 20% Pd(OH)$_2$/C (40 mg) as in Example 3, Step E, in the presence of 2N HCl in ether (0.20 mL) to afford the title product HCl salt after filtration and evaporation of solvent. HPLC/MS: m/e=519 (M+1), Rt=3.21 min.

EXAMPLE 14

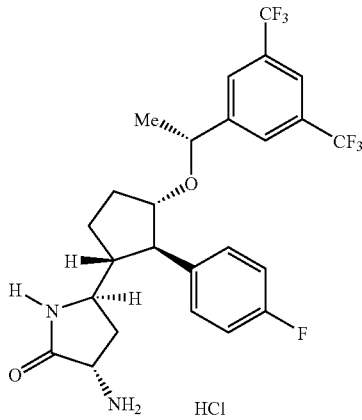

(3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-aminopyrrolidin-2-one hydrochloride salt Using essentially the same procedures as in Example 13, Steps B-C, but starting with the minor, lower mesylate (3R,5R)-5-(((1R),(2R),(3S))-3-((1R)-1-(3,5-bis(trifluoromethyl)phenyl)ethoxy)-2-(4-fluorophenyl)cyclopentan-1-yl)-3-mesylpyrrolidin-2-one from Step A, the title product was obtained. HPLC/MS: m/e=519 (M+1), Rt=3.21 min. Azide intermediate NMR (CDCl$_3$): δ 1.40 (d, J=6.4 Hz, 3 H), 1.68-1.78 (m, 1 H), 1.78-1.91 (m, 3 H), 1.91-1.98 (m, 1 H), 1.98-2.06 (m, 1 H), 2.10-2.18 (m, 1 H), 2.75 (dd, J=7.5 and 10.5 Hz, 1 H), 3.65 (br q, 1 H), 3.72 (q, J=6.0 Hz, 1 H), 4.04 (dd, J=5.9 and 8.2 Hz, 1 H), 4.51 (q, J=6.4 Hz, 1 H), 6.97 (br t, J=8.7 Hz, 2 H), 7.07-7.13 (m, 2 H), 7.45 (s, 2 H), 7.67 (br s, 1 H), 7.71 (s, 1 H).

EXAMPLE 15

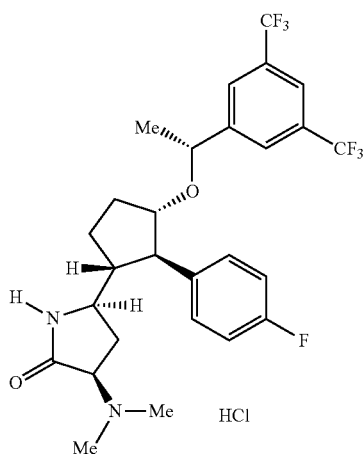

(3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-dimethylaminopyrrolidin-2-one hydrochloride salt To a solution of (3R,5R)-5-(((1R),(2R),(3S))-3-((1R)-1-(3,5-bis(trifluoromethyl)phenyl)-ethoxy)-2-(4-fluorophenyl)cyclopentan-1-yl)-3-aminopyrrolidin-2-one (20 mg, 0.036 mmol) from Example 13 in 1,2-dichloroethane (1 mL) was added 37% by wt aq formaldehyde (0.015 mL), DIPEA (0.0063 mL), and sodium triacetoxy borohydride (23 mg) and the reaction was stirred at rt for 16 hr. The mixture was diluted with water and extracted twice with methylene chloride. The organic layers were each successively washed with brine containing some sodium carbonate solution, combined, and dried over sodium sulfate. Removal of solvent in vacuo and purification by Prep TLC (5% methanol/methylene chloride) afforded the title compound after formation of the hydrochloride salt with 2N HCl in ether and evaporation. HPLC/MS: m/e=547 (M+1), Rt=3.23 min. NMR (CDCl₃): δ 1.39 (d, J=6.6 Hz, 3 H), 1.38-1.47 (m, 1 H), 1.74-1.88 (m, 2 H), 1.93-2.05 (m, 3 H), 2.05-2.16 (m, 1 H), 2.10-2.18 (m, 1 H), 2.35 (s, 6 H), 2.78 (dd, J=7.5 and 10 Hz, 1 H), 3.4-3.5 (m, 2 H), 3.69 (m, 1 H), 4.51 (q, J=6.6 Hz, 1 H), 6.96 (br t, J=8.7 Hz, 2 H), 7.04-7.08 (m, 2 H), 7.33 (br s, 1 H), 7.44 (s, 2 H), 7.71 (s, 1 H).

EXAMPLE 16

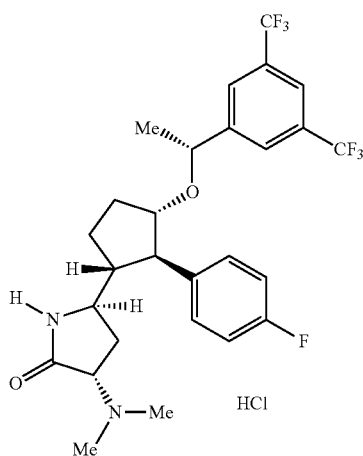

(3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-dimethylaminopyrrolidin-2-one hydrochloride salt Using essentially the same procedures as in Example 15, but starting with (3S,5R)-5-(((1R),(2R),(3S))-3-((1R)-1-(3,5-bis(trifluoromethyl)phenyl)ethoxy)-2-(4-fluorophenyl)cyclopentan 1-yl)-3-dimethylaminopyrrolidin-2-one from Example 14, the title product was obtained. HPLC/MS: m/e=519 (M+1), Rt=3.21 min.

EXAMPLE 17

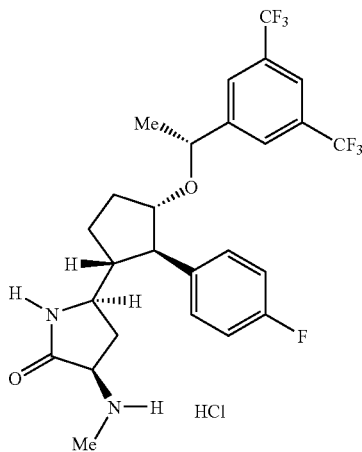

(3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-methylaminopyrrolidin-2-one hydrochloride salt A solution of (3R,5R)-5-(((1R),(2R),(3S))-3-((1R)-1-(3,5-bis(trifluoromethyl)phenyl)-ethoxy)-2-(4-fluorophenyl)cyclopentan-1-yl)-3-aminopyrrolidin-2-one (25 mg, 0.048 mmol) prepared as in Example 13, 1-hydroxymethylbenztriazole (7.2 mg), and DIPEA (0.017 mL) were stirred in methanol (2 mL) for 16 hrs and was then evaporated. The residue was taken up in methanol (2 mL) and hydrogenated for 2 hr at 45 psi over 20% Pd(OH)₂/C (40 mg) as in Example 3, Step E. HPLC/MS indicated a mixture of starting material, mono- and di-methylation. The title compound was isolated by RP prep HPLC and converted to the hydrochloride salt with 2N HCl in ether.

HPLC/MS: m/e=533 (M+1), Rt=3.25 min.

EXAMPLE 18

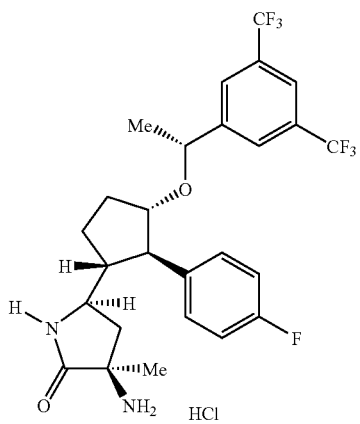

(3R,5R)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt

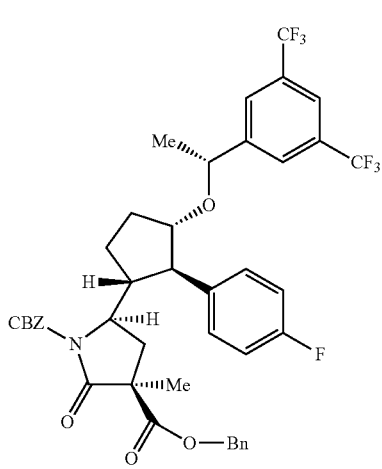

Step A: (3R,5R)-5-(((1R),(2R),(3S))-3-((1R)-1-(3,5-bis(Trifluoromethyl)phenyl)ethoxy)-2-(4-fluorophenyl)cyclopent-1-yl)-1,3-dibenzyloxycarbonyl-3-methylpyrrolidin-2-one A solution of (5R)-5-(((1R),(2R),(3S))-3-((1R)-1-(3,5-bis(trifluoromethyl)phenyl)-ethoxy)-2-(4-fluorophenyl)cyclopentan-1-yl)-1-benzyloxycarbonylpyrrolidin-2-one (13 gm, 20.4 mmol) (prepared as in Example 3, Step D, (dried by prior evaporation of 100 mL of toluene) in THF (200 mL) under nitrogen was cooled to −25° C. in an ice/dry ice/methanol bath and benzyl chloroformate (3.2 mL) was added. After stirring for 10 min, 1M NaHMDS (51 mL) was added slowly over 10 min. The reaction was allowed to warm to −15° C. over 30 min at which time TLC (30% ethyl acetate/hexanes) of an aliquot (quenched into ethyl acetate/2N HCl) indicated that the starting material was essentially gone. Methyl iodide (12.7 mL) was added and the reaction was allowed to warm to rt for 1 hr and was then warmed in a water bath to 30° C. for 2-3 hr. The reaction was monitored by HPLC/MS for the intermediate (m/e=728 (M+1-44, 100%), Rt=4.64 min) and product (m/e=742 (M+1-44, 100%), Rt=4.69 min) and was about 90% complete. The reaction was then stored at 0° C. overnight at which time the methylation was deemed essentially complete and the reaction was slowly quenched into a stirred mixture of ethyl acetate, water, and excess 2N HCl solution. The mixture was extracted twice with ethyl acetate and the ethyl acetate layers were each successively washed with brine containing some sodium bicarbonate solution, combined, and dried over sodium sulfate. Removal of solvent in vacuo and purification by FC (10-50% ethyl acetate/hexanes) afforded the title intermediate. The (5S) isomer (5-10%) is slightly higher Rf and was normally only partially separated at this step since it can be removed in subsequent steps. However on smaller scale, the minor, higher Rf isomer can be isolated.

HPLC/MS: m/e=742 (M+1-44, 100%), 786 (M+1); Rt=4.69 min NMR (CDCl$_3$) (Major, lower (3R,5R) isomer): δ 1.37 (d, J=6.6 Hz, 3 H), 1.48 (s, 3 H), 1.58-1.66 (m, 1 H), 1.71-1.85 (m, 2 H), 1.95-2.05 (m, 2 H), 2.50 (dd, J=6.6 and 12 Hz, 1 H), 2.84-2.92 (m, 1 H), 2.86 (dd, J=6.6 and 10 Hz, 1 H), 3.59 (q, J=6.4 Hz, 1 H), 4.33 (br q, J=7 Hz, 1 H), 4.48 (q, J=6.6 Hz, 1 H), 4.76 and 4.98 (ABq, J=12.5 Hz, 2 H), 5.22 and 5.25 (ABq, J=11 Hz, 2 H), 6.73-6.83 (m, 4 H), 7.3-7.46 (m, 5 H), 7.42 (s, 2 H), 7.69 (s, 1 H).

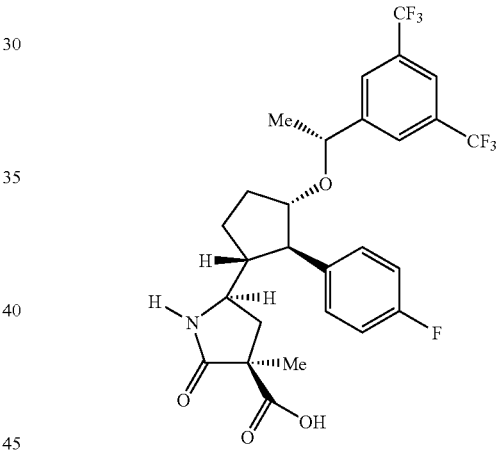

Step B: (3R,5R)-5-(((1R),(2R),(3S))-3-((1R)-1-(3,5-bis(Trifluoromethyl)phenyl)ethoxy)-2-(4-fluorophenyl)cyclopent-1-yl)-3-carboxy-3-methylpyrrolidin-2-one A solution of (3R,5R)-5-(((1R),(2R),(3S))-3-((1R)-1-(3,5-bis(trifluoromethyl)phenyl)-ethoxy)-2-(4-fluorophenyl)cyclopent-1-yl)-1,3-dibenzyloxycarbonyl-3-methylpyrrolidin-2-one (22.5 gm, 28.7 mmol) (prepared as in Step A) in methanol (500 mL) was hydrogenated over 20% Pd(OH)$_2$/C (2.0 gm) on a Parr shaker at 45 p.s.i. in a 2 L flask. After 6 hr, HPLC/MS indicated mostly product acid (m/e=562 (M+1), Rt=3.89 min) and a trace of methyl ester (m/e=576 (M+1), Rt=4.13 min), but still some intermediate benzyl ester (m/e=652 (M+1), Rt=4.38 min). Thus, an additional portion of 20% Pd(OH)$_2$/C (0.5 gm) was added and the hydrogenation was continued for another 16 hr, at which time HLPC/MS indicated that the hydrogenation was essentially complete. The reaction was filtered to remove catalyst and was evaporated to dryness to afford the title acid. This material was routinely used without purification after evaporating a portion of toluene to remove residual water and methanol. A portion was recrystallized from ethyl acetate/heptanes and then again from nitromethane to afford x-ray quality crystals which confirmed the indicated stereochemistries. HPLC/MS: m/e=562 (M+1); Rt=3.89 min NMR (CDCl₃)(Major (3R,5R) isomer): δ 1.39 (d, J=6.6 Hz, 3 H), 1.47 (s, 3 H), 1.64-1.76 (m, 1 H), 1.76-1.87 (m, 1 H), 1.87-2.01 (m, 2 H), 2.01-2.11 (m, 2 H), 2.11-2.18 (m, 1 H), 2.75 (dd, J=6.5 and 9.4 Hz, 1 H), 3.63 (t, J=5.4 Hz, 1 H), 3.69 (m, 1 H), 4.50 (q, J=6.6 Hz, 1 H), 6.67 (br s, 1 H), 6.93 (m, 2 H), 6.98 (m, 2 H), 7.44 (s, 2 H), 7.69 (s, 1 H).

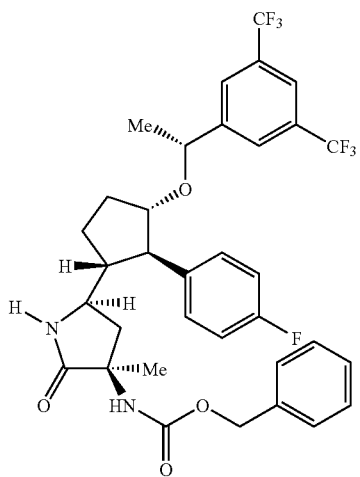

Step C: (3R,5R)-5-(((1R),(2R),(3S))-3-((1R)-1-(3,5-bis(Trifluoromethyl)phenyl)ethoxy)-2-(4-fluorophenyl)cyclopent-1-yl)-3-benzyloxycarbonylamino-3-methylpyrrolidin-2-one To a solution of (3R,5R)-5-(((1R),(2R),(3S))-3-((1R)-1-(3,5-bis(trifluoromethyl)phenyl)-ethoxy)-2-(4-fluorophenyl)cyclopent-1-yl)-3-carboxy-3-methylpyrrolidin-2-one (15 gm, 26.7 mmol) (prepared as in Step B and dried by evaporation of 100 mL of toluene) in acetone (200 mL) was added at rt DIPEA (12 mL) and then isobutyl chloroformate (5.25 mL). The reaction was stirred at rt for 40 min and was then cooled to 0° C. in an ice/brine bath. This solution was slowly added to a cold solution of sodium azide (8.7 gm) in water (150 mL) and acetone (150 mL) maintaining the temperature at <10° C. The mixture was stirred for 45 min (HPLC/MS indicated some acid, but mostly acyl azide, m/e=587 (M+1), Rt=4.22) and then most of the acetone was removed in vacuo without heating. The mixture was diluted with ice water and was extracted twice with toluene. The toluene layers were each successively washed with cold brine containing some sodium bicarbonate solution, combined, and dried over sodium sulfate. About ⅔ of the solvent was removed in vacuo without heating to afford a dry toluene solution of the acyl azide intermediate. (Note: It is very important to keep the solution cold to prevent rearrangement to the isocyanate prior to complete drying by azeotroping any water and acetone during removal of the toluene. Also, the residual isobutanol must be removed at this time. However, the acyl azide should not be concentrated to dryness due to the exothermic loss of nitrogen during the subsequent rearrangement.) The above toluene solution of acyl azide (~200 mL) was heated to 85° C. under nitrogen for 1-2 hr (nitrogen bubbling ceases and HPLC/MS indicated acyl azide was gone, isocyanate m/e=559 (M+1), Rt=4.29 min) and was then further concentrated to 100 mL. To this solution was added benzyl alcohol (28 mL), DIPEA (14 mL), and DMAP (200 mg, cat) and the mixture was reheated to 85° C. for 3-4 hr (monitored by HPLC/MS for loss of isocyanate, m/e=559 (M+1), Rt=4.29 min; product, m/e=667 (M+1), Rt=4.23 min). The mixture was concentrated in vacuo and purified by FC (20-80% ethyl acetate/hexanes) to remove some of the residual (3S,5S) and (3R,5S) isomers and afforded the title intermediate (>95% (3R,5R) isomer). Any residual amounts of (3S,5S) and (3R,5S) isomers were removed by preparative reverse phase HPLC (0.1% TFA in 70% acetonitrile/water). The product fractions were combined, sodium bicarbonate added to neutralize TFA, acetonitrile was mostly removed in vacuo, the product was extracted from the aqueous with 2× ethyl acetate, and the solvent was evaporated after drying with sodium sulfate to afford the title CBZ intermediate (10 gm) and 2.8 gm mixed fractions after the main isomer peak. The mixed fractions could be further purified by Chiracel OD to obtain additional product (Rt=8 min), as well as the minor (3S,5R) isomer (Rt=22.5 min) and variable amounts of the (3S,5S) isomer (Rt=10.5 min). NMR (CDCl₃) (Major, (3R,5R) isomer): δ 1.37 (s, 3 H), 1.40 (d, J=6.4 Hz, 3 H), 1.78-1.9 (m, 2 H), 1.91-2.0 (m, 1 H), 2.0-2.25 (m, 3 H), 2.79 (dd, J=6.6 and 12 Hz, 1 H), 3.52-3.61 (m, 1 H), 3.65 (q, J=6.4 Hz, 1 H), 4.52 (q, J=6.6 Hz, 1 H), 5.05 and 5.09 (ABq, 2 H), 5.29 (br s, 1 H), 6.23 (br s, 1 H), 6.96 (br t, 2 H), 7.04 (br m, 2 H), 7.32-7.41 (m, 5 H), 7.47 (s, 2 H), 7.72 (s, 1 H). NMR (CDCl₃) (Minor, (3S,5R) isomer): δ 1.26 (s, 3 H), 1.36 (d, J=6.5 Hz, 3 H), 1.50 (dd, 1 H), 1.6-1.73 (m, 1 H), 1.73-1.85 (m, 1 H), 1.85-2.3 (m, 4 H), 2.47 (dd, J=6.6 and 12 Hz, 1 H), 2.67 (dd, J=6.6 and 12 Hz, 1 H), 3.61 (q, J=6.3 Hz, 1 H), 3.80 (br s, 1 H), 4.46 (q, J=6.4 Hz, 1 H), 4.99 and 5.05 (ABq, J=12.2 Hz, 1 H), 6.12 (br s, 1 H), 6.92 (br t, 2 H), 6.98 (br m, 2 H), 7.26-7.38 (m, 5 H), 7.40 (s, 2 H), 7.66 (s, 1 H). NMR (CDCl₃) (lactam (3S,5S) isomer): δ 1.34 (s, 3 H), 1.36 (d, J=6.5 Hz, 3 H), 1.55-1.71 (m, 1 H), 1.71-1.84 (m, 1 H), 1.84-1.95 (m, 1 H), 1.95-2.2 (m, 3 H), 2.47 (dd, J=6.6 and 12 Hz, 1 H), 2.73 (t, 1 H), 3.45 (q, J=6.3 Hz, 1 H), 3.64 (m, 1 H), 4.44 (q, J=6.4 Hz, 1 H), 4.97 (br s, 1 H), 5.03 and 5.08 (ABq, 1 H), 5.32 (br s, 1 H), 6.95 (br t, 2 H), 7.05 (br m, 2 H), 7.28-7.38 (m, 5 H), 7.36 (s, 2 H), 7.66 (s, 1 H).

Step D: (3R,5R)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt A solution of (3R,5R)-5-(((1R),(2R),(3S))-3-((1R)-1-(3,5-bis(trifluoromethyl)-phenyl)ethoxy)-2-(4-fluorophenyl)cyclopent-1-yl)-3-benzyloxycarbonylamino-3-methylpyrrolidin-2-one (12.5 gm, 18.7 mmol) (prepared as in Step C) in methanol (100 mL) and 2N HCl in ether (19 mL) was hydrogenated over 20% Pd(OH)₂/C (0.65 gm) on a Parr shaker at 45 p.s.i. for 90 min. HPLC/MS indicated product (m/e=533 (M+1), Rt=3.33 min) and only a trace of N-methylation (m/e=547 (M+1), Rt=3.35 min). The reaction was filtered to remove catalyst and was evaporated to dryness to afford the title compound as the hydrochloride salt. This material was triturated three times with ether (200 mL each) to afford the final product as a white solid (10.2 gm) after vacuum drying. HPLC/MS: m/e=532 (M+1); Rt=3.25 min NMR (CD₃OD) (Major (3R,5R) isomer): δ 1.31 (d, J=6.5 Hz, 3 H), 1.35 (s, 3 H), 1.46 (dd, J=9.3 and 12.6 Hz, 1 H), 1.67-1.84 (m, 2 H), 1.93-2.08 (m, 3 H), 2.14-2.23 (m, 1 H), 2.79 (dd, J=6.6 and 12 Hz, 1 H), 3.59 (dt, 1 H), 3.72 (q, J=7.6 Hz, 1 H), 4.62 (q, J=6.6

Hz, 1 H), 6.91 (m, 2 H), 7.13 (m, 2 H), 7.50 (s, 2 H), 7.70 (s, 1 H). Use of nOe experiments confirmed the relative lactam stereochemistry as (3R,5R).

EXAMPLE 19

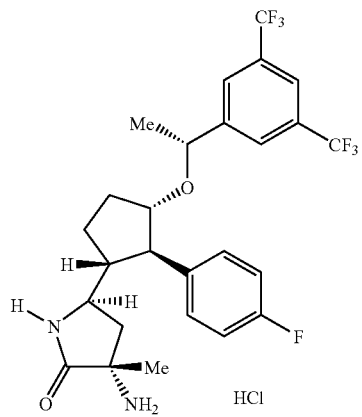

(3S,5R)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt Using essentially the same procedures as in Example 18, but using the higher Rf (3S,5R)-5-(((1R),(2R),(3S))-3-((1R)-1-(3,5-bis(trifluoromethyl)phenyl)ethoxy)-2-(4-fluorophenyl)cyclopent-1-yl)-1,3-dibenzyloxyarbonyl-3-methylpyrrolidin-2-one from Step A or the slower (3S,5R)-5-(((1R),(2R),(3S))-3-((1R)-1-(3,5-bis(trifluoromethyl)phenyl)ethoxy)-2-(4-fluorophenyl)cyclopent-1-yl)-3-benzyloxycarbonylamino-3-methylpyrrolidin-2-one (Rt=22.5 min) from Step C, the title product was obtained. HPLC/MS: m/e=532 (M+1); Rt=3.26 min

EXAMPLE 20

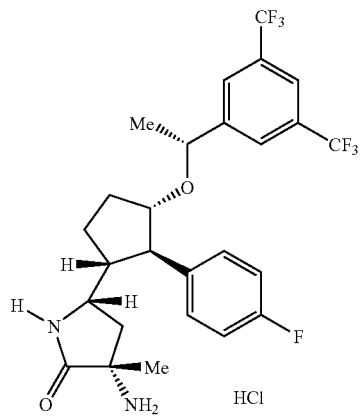

(3S,5S)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt Using essentially the same procedures as in Example 18, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonylpyrrolidin-2-one from Example 4 or using the middle (3S,5S)-5-(((1R),(2R),(3S))-3-((1R)-1-(3,5-bis(trifluoromethyl)phenyl)ethoxy)-2-(4-fluorophenyl)cyclopent-1-yl)-3-benzyloxycarbonylamino-3-methylpyrrolidin-2-one (Rt=10.5 min) from Example 18, Step C, the title product was obtained. HPLC/S: m/e=532 (M+1); Rt=3.26 min

EXAMPLE 21

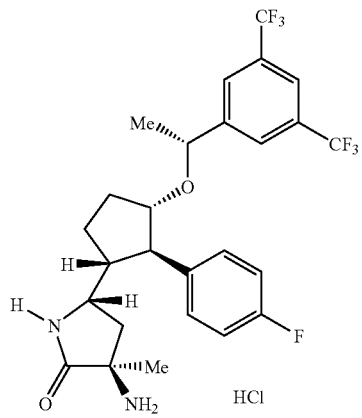

(3R,5S)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt Using essentially the same procedures as in Example 18, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonylpyrrolidin-2-one from Example 4 and using the faster (3R,5S)-5-(((1R),(2R),(3S))-3-((1R)-1-(3,5-bis(trifluoromethyl)phenyl)ethoxy)-2-(4-fluorophenyl)cyclopent-1-yl)-3-benzyloxycarbonylamino- 3-methylpyrrolidin-2-one (Rt=8.2 min) as in Example 18, Step C, the title product was obtained. HPLC/MS: m/e=532 (M+1); Rt=3.26 min

EXAMPLE 22

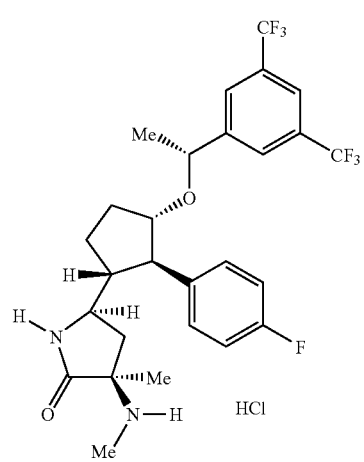

(3R,5R)-5-(((1R),(2R),(3S))-3-((1R)-1-(3,5-bis(Trifluoromethyl)phenyl)ethoxy)-2-(4-fluorophenyl)-cyclopent-1-yl)-3-aminomethyl-3-methylpyrrolidin-2-one hydrochloride salt Using essentially the same procedures as in Example 17, but starting with (3R,5R)-5-(((1R),(2R),(3S))-3-((1R)-1-(3,5-bis(1-difluoromethyl)phenyl)ethoxy)-2-(4-fluorophenyl) cyclopent-1-yl)-3-amino-3-methylpyrrolidin-2-one hydrochloride salt (30 mg) from Example 18, the title compound was obtained. HPLC/MS: m/e=547 (M+1); Rt=3.28 min

EXAMPLE 23

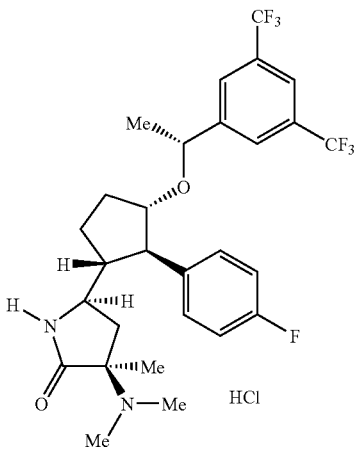

(3R,5R)-5-(((1R),(2R),(3S))-3-((1R)-1-(3,5-bis(Trifluoromethyl)phenyl)ethoxy)-2-(4-fluorophenyl)cyclopent-1-yl)-3-dimethylamino-3-methylpyrrolidin-2-one hydrochloride salt Using essentially the same procedures as in Example 16, but starting with (3R,5R)-5-(((1R),(2R),(3S))-3-((1R)-1-(3,5-bis(trifluoromethyl)phenyl)ethoxy)-2-(4-fluorophenyl)cyclopent-1-yl)-3-amino-3-methylpyrrolidin-2-one hydrochloride salt (30 mg) from Example 18, the title compound was obtained. HPLC/MS: m/e=561 (M+1); Rt=3.31 min While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A pharmaceutical composition for the treatment of a disease selected from urinary frequency, urinary urgency and urinary incontinence wherein there are exactly two active agents:
   (R)-N-[4-[2-[[2-hydroxy-2-(pyridin-3-yl)ethyl]amino]ethyl]phenyl]-4-[4-(4-trifluoromethylphenyl)thiazol-2-yl]benzenesulfonamide or a salt thereof, and tolterodine.

2. Method of treating urinary frequency, urinary urgency or urinary incontinence in a patient in need of such treatment comprising: administering to said patient a therapeutically effective amount of a composition according to claim 1.

\* \* \* \* \*